US012193791B2

(12) United States Patent
Wang et al.

(10) Patent No.: US 12,193,791 B2
(45) Date of Patent: Jan. 14, 2025

(54) HANDHELD DEVICE FOR PHOTOACOUSTIC MICROSCOPY AND RELATED PHOTOACOUSTIC MICROSCOPY SYSTEM

(71) Applicant: City University of Hong Kong, Kowloon (HK)

(72) Inventors: Lidai Wang, Kowloon (HK); Jiangbo Chen, Kowloon (HK)

(73) Assignee: City University of Hong Kong, Kowloon (HK)

( * ) Notice: Subject to any disclaimer, the term of this patent is extended or adjusted under 35 U.S.C. 154(b) by 299 days.

(21) Appl. No.: 17/881,941

(22) Filed: Aug. 5, 2022

(65) Prior Publication Data

US 2024/0041329 A1 Feb. 8, 2024

(51) Int. Cl.
*A61B 5/00* (2006.01)
*A61B 8/00* (2006.01)
*G01N 29/24* (2006.01)

(52) U.S. Cl.
CPC .......... *A61B 5/0095* (2013.01); *A61B 5/0035* (2013.01); *A61B 5/0068* (2013.01); *A61B 8/4427* (2013.01); *A61B 8/4461* (2013.01); *G01N 29/2418* (2013.01)

(58) Field of Classification Search
CPC ....... A61B 5/00; A61B 5/0035; A61B 5/0068; A61B 5/0095; A61B 8/4427; A61B 8/4461; G01N 29/24; G01N 29/2418
See application file for complete search history.

(56) References Cited

U.S. PATENT DOCUMENTS

| 2018/0303349 | A1* | 10/2018 | Wang | A61B 5/0095 |
| 2022/0137397 | A1* | 5/2022 | Zou | B81B 3/0018 |
| | | | | 359/224.1 |

FOREIGN PATENT DOCUMENTS

| CN | 104323762 A | * | 2/2015 | ........... A61B 5/0035 |
| CN | 110584615 A | * | 12/2019 | ............... A61B 5/00 |
| CN | 115089117 A | * | 9/2022 | ............... A61B 5/00 |
| CN | 115128009 A | * | 9/2022 | ............. G01N 21/17 |

OTHER PUBLICATIONS

Machine translation of CN-104323762-A (Year: 2015).*
Machine translation of CN-115128009-A (Year: 2022).*
(Continued)

*Primary Examiner* — Nguyen Q. Ha
(74) *Attorney, Agent, or Firm* — Renner, Kenner, Greive, Bobak, Taylor & Weber

(57) ABSTRACT

A handheld device for photoacoustic microscopy. The handheld device includes an optical assembly, a light beam scanner and a transducer unit. The optical assembly is arranged to provide a light beam. The light beam scanner includes a reflector arranged to reflect the light beam from the optical assembly to provide a reflected light beam to an object, a first drive mechanism operable to move the reflector relative to the optical assembly to move the reflected light beam relative to the object, and a second drive mechanism operable to move the reflector relative to the optical assembly to move the reflected light beam relative to the object. The transducer unit is arranged to detect photoacoustic signals emitted by the object in response to receiving the reflected light beam.

31 Claims, 23 Drawing Sheets

(56) References Cited

OTHER PUBLICATIONS

Machine Translation of CN-110584615-A (Year: 2019).*
Machine Translation of CN-115089117-A (Year: 2022).*
Voskuil, F. J. et al. Intraoperative imaging in pathology-assisted surgery. Nat. Biomed. Eng. 1-12 (2021) doi:10.1038/s41551-021-00808-8.
Heeman, W. et al. A guideline for clinicians performing clinical studies with fluorescence imaging. J. Nucl. Med. 63, numed.121.262975 (2022).
Wang, L. V. & Yao, J. A practical guide to photoacoustic tomography in the life sciences. Nat. Methods 13, 627-638 (2016).
Yao, J. & Wang, L. V. Photoacoustic microscopy. Laser Photonics Rev. 7, 758-778 (2013).
Yao, J. & Wang, L. V. Sensitivity of photoacoustic microscopy. Photoacoustics 2, 87-101 (2014).
Wang, L., Zhang, C. & Wang, L. V. Grueneisen relaxation photoacoustic microscopy. Phys. Rev. Lett. 113, 1-5 (2014).
Jeon, S., Kim, J., Lee, D., Baik, J. W. & Kim, C. Review on practical photoacoustic microscopy. Photoacoustics 15, 100141 (2019).
Park, J. et al. Quadruple ultrasound, photoacoustic, optical coherence, and fluorescence fusion imaging with a transparent ultrasound transducer. Proc. Natl. Acad. Sci. U. S. A. 118, 1-12 (2021).
Zhou, H. C. et al. Optical-resolution photoacoustic microscopy for monitoring vascular normalization during anti-angiogenic therapy. Photoacoustics 15, 100143 (2019).
Cheng, S. et al. High-resolution photoacoustic microscopy with deep penetration through learning. Photoacoustics 25, 100314 (2022).
Liu, C., Chen, J., Zhang, Y., Zhu, J. & Wang, L. Five-wavelength optical-resolution photoacoustic microscopy of blood and lymphatic vessels. Adv. Photonics 3, 1-9 (2021).
Liu, C., Liang, Y. & Wang, L. Photoacoustics Single-shot photoacoustic microscopy of hemoglobin concentration, oxygen saturation, and blood flow in sub-microseconds. Photoacoustics 17, 100156 (2020).
Zhu, J. et al. Self-fluence-compensated functional photoacoustic microscopy. IEEE Trans. Med. Imaging PP, 1 (2021).
Chen, J. et al. Dual-foci fast-scanning photoacoustic microscopy with 3.2-MHz A-line rate. Photoacoustics 23, 100292 (2021).
Hu, S. et al. Optical-resolution photoacoustic microscopy of ischemic stroke. Photons Plus Ultrasound Imaging Sens. 2011 7899, 789906 (2011).
Hu, S., Maslov, K. & Wang, L. V. Second-generation optical-resolution photoacoustic microscopy with improved sensitivity and speed. Opt. Lett. 36, 1134 (2011).
Chen, J. et al. Confocal Visible/NIR Photoacoustic Microscopy of Tumor with Structural, Functional and Nanoprobe Contrasts. Photonics Res. 8, (2020).
Wang, L., Maslov, K., Yao, J., Rao, B. & Wang, L. V. Fast voice-coil scanning optical-resolution photoacoustic microscopy. Opt. Lett. 36, 139-141 (2011).
Chen, J., Zhang, Y., He, L., Liang, Y. & Wang, L. Wide-field polygon-scanning photoacoustic microscopy of oxygen saturation at 1-MHz A-line rate. Photoacoustics 20, 100195 (2020).
Lan, B. et al. High-speed widefield photoacoustic microscopy of small-animal hemodynamics. Biomed. Opt. Express 9, 1689 (2018).
Yao, J. et al. Wide-field fast-scanning photoacoustic microscopy based on a water-immersible MEMS scanning mirror. J. Biomed. Opt. 17, 1 (2012).
Yao, J. et al. functional photoacoustic microscopy of mouse brain in action. Nat. Methods 1-7 (2015) doi:10.1038/nmeth.3336.
Park, K. et al. Handheld photoacoustic microscopy probe. Sci. Rep. 7, 1-15 (2017).
Chen, M. et al. Photoacoustics High-speed functional photoacoustic microscopy using a water-immersible two-axis torsion-bending scanner. Photoacoustics 100309 (2021) doi:10.1016/j.pacs.2021.100309.
Qin, W., Chen, Q. & Xi, L. A handheld microscope integrating photoacoustic microscopy and optical coherence tomography. Biomed. Opt. Express 9, 2205 (2018).
Zhang, W. et al. High-speed dual-view photoacoustic imaging pen. Opt. Lett. 45, 1599 (2020).
Lin, L. et al. Handheld optical-resolution photoacoustic microscopy. J. Biomed. Opt. 22, 041002 (2016).
Chen, Q., Qin, W., Qi, W. & Xi, L. Progress of clinical translation of handheld and semi-handheld photoacoustic maging. Photoacoustics 22, 100264 (2021).
Cao, R. et al. Hemodynamic and oxygen-metabolic responses of the awake mouse brain to hypercapnia revealed by multi-parametric photoacoustic microscopy. J. Cereb. Blood Flow Metab. 41, 2628-2639 (2021).
Hu, S., Maslov, K. & Wang, L. V. In vivo functional chronic imaging of a small animal model using optical-resolution photoacoustic microscopy. Med. Phys. 36, 2320-2323 (2009).
Xu, S., Duan, X. & Zou, J. A Two-Axis Water-Immersible Micro Scanning Mirror Driven by Single Inductor Coil through Dynamic Structural Filtering. Sensors Actuators, A Phys. 284, 172-180 (2018).
Huang, C. H., Yao, J., Wang, L. V. & Zou, J. A water-immersible 2-axis scanning mirror microsystem for ultrasound andha photoacoustic microscopic imaging applications. Microsyst. Technol. 19, 577-582 (2013).
Young Kim, J., Lee, C., Park, K., Lim, G. & Kim, C. A PDMS-based 2-axis waterproof scanner for photoacoustic microscopy. Sensors (Switzerland) 15, 9815-9826 (2015).
Xu, S., Li, S. & Zou, J. A micromachined water-immersible scanning mirror using BoPET hinges. Sensors Actuators, A Phys. 298, 111564 (2019).
Xu, S., Huang, C.-H. & Zou, J. Microfabricated water-immersible scanning mirror with a small form factor for handheld ultrasound and photoacoustic microscopy. J. Micro/Nanolithography, MEMS, MOEMS 14, 035004 (2015).
Singla, S. & Sharma, R. Medical Image Stitching Using Hybrid of Sift & Surf Techniques. Int. J. Adv. Res. Electron. Commun. Eng. 3, 838-842 (2014).
Li, Y., Wang, Y. & Huang, W. Automatic image stitching using SIFT. ICALIP 2008—2008 Int. Conf. Audio, Lang. Image Process. Proc. 568-571 (2008) doi:10.1109/ICALIP.2008.4589984.
Domokos, C. & Kato, Z. Parametric estimation of affine deformations of planar shapes. Pattern Recognit. 43, 569-578 (2010).
Zhang, Z. A flexible new technique for camera calibration. IEEE Trans. Pattern Anal. Mach. Intell. 22, 1330-1334 (2000).

* cited by examiner

HANDHELD DEVICE FOR PHOTOACOUSTIC MICROSCOPY AND RELATED PHOTOACOUSTIC MICROSCOPY SYSTEM

TECHNICAL FIELD

The invention relates to a handheld device for photoacoustic microscopy and a related photoacoustic microscopy system.

BACKGROUND

Photoacoustic microscopy is a hybrid imaging technique based on the photoacoustic effect. Generally, in photoacoustic microscopy, an object is irradiated with a light (e.g., laser) beam. The object absorbs at least some of the energy of the light beam, then heats up and induces an initial pressure changes which propagates through the object as acoustic (photoacoustic) waves. By recording these acoustic waves over a surface of the object, structural and/or functional images of the object can be reconstructed.

One specific type of photoacoustic microscopy is optical-resolution photoacoustic microscopy, with optical focusing tighter than acoustic focusing. Optical-resolution photoacoustic microscopy may enable non-invasive, label-free hemodynamic and functional imaging with high sensitivity. However, some existing systems for performing optical-resolution photoacoustic microscopy suffer from one or more of these problems: limited field of view (e.g., limited to a few millimeters, which may be insufficient for some applications), uses bulky scanners/scan probes (which may not be readily used for some applications), slow imaging speed (which may be insufficient for some applications), etc.

SUMMARY OF THE INVENTION

In a first aspect of the invention, there is provided a handheld device for photoacoustic microscopy. The handheld device includes an optical assembly, a light beam scanner, and a transducer unit. The optical assembly is arranged to provide a light beam. The light beam scanner includes a reflector arranged to reflect the light beam from the optical assembly to provide a reflected light beam to an object, a first drive mechanism operable to move the reflector relative to the optical assembly to move the reflected light beam relative to the object, and a second drive mechanism operable to move the reflector relative to the optical assembly to move the reflected light beam relative to the object. The transducer unit is for detecting photoacoustic signals emitted by the object in response to receiving the reflected light beam. The handheld device may be used for freehand photoacoustic microscopy.

For example, the handheld device may be used for optical-resolution photoacoustic microscopy. For example, the handheld device may be used for intraoperative photoacoustic microscopy. For example, the handheld device may be used for structural and/or functional photoacoustic microscopy of an object. For example, the handheld device may be used for one or more of: in vivo photoacoustic microscopy, ex vivo photoacoustic microscopy, in vitro photoacoustic microscopy, etc. The object may be an animal, a human, a phantom, a tissue sample, etc.

Optionally, the first drive mechanism is a first type of drive mechanism, and the second drive mechanism is a second type of drive mechanism different from the first type. Example types of first drive mechanism include MEMS based drive mechanism, galvanometer based drive mechanism, resonance (e.g., voice coil) based drive mechanism, piezoelectric based drive mechanism, solid state based drive mechanism, etc. Example types of second drive mechanism include MEMS based drive mechanism, galvanometer based drive mechanism, resonance (e.g., voice coil) based drive mechanism, piezoelectric based drive mechanism, solid state based drive mechanism, etc.

Optionally, the first drive mechanism and the second drive mechanism are operable independently. The first drive mechanism and the second drive mechanism may be operated separately. The first drive mechanism and the second drive mechanism may be operated simultaneously.

Optionally, the first drive mechanism is operable to rotate the reflector about a first axis, e.g., to move the reflected light beam along a first scan axis. In one example, the first drive mechanism is operable to oscillate the reflector about the first axis.

Optionally, the second drive mechanism is operable to rotate the reflector about a second axis, e.g., to move the reflected light beam along a second scan axis. In one example, the second drive mechanism is operable to oscillate the reflector about the second axis. The first axis is different from the second axis. The first scan axis is different from the second scan axis.

The first axis and the second axis may be arranged at an angle (with or without crossing of the two axes in 3D space). For example, the first axis and the second axis are substantially orthogonal.

The first scan axis and the second scan axis may be arranged at an angle. For example, the first scan axis and the second scan axis are substantially orthogonal.

Optionally, the first drive mechanism is arranged or controlled to move the reflector at a first rate, and the second drive mechanism is arranged or controlled to move the reflector at a second rate different from (faster than or slower than) the first rate.

Optionally, the first drive mechanism is arranged or controlled to move the reflector to provide a scanning range along the first scan axis in the order of millimeters. Optionally, the second drive mechanism is arranged or controlled to move the reflector to provide a scanning range along the second scan axis in the order of millimeters. Optionally, the scanning range along the first scan axis is different from (larger than or smaller than) the scanning range along the second scan axis.

Optionally, the first drive mechanism is arranged or controlled to move the reflector to provide a scanning step size along the first scan axis in the order of micrometers. Optionally, the second drive mechanism is arranged or controlled to move the reflector to provide a scanning step size along the second scan axis in the order of micrometers. Optionally, the scanning step size along the first scan axis is different from (larger than or smaller than) the scanning step size along the second scan axis.

Optionally, the first drive mechanism comprises one of a galvanometer-based drive mechanism and a resonance-based drive mechanism, and the second drive mechanism comprises another one of the galvanometer-based drive mechanism and the resonance-based drive mechanism.

Optionally, the galvanometer-based drive mechanism comprises a galvanometer-based motor (e.g., a single galvanometer-based motor).

Optionally, the resonance-based drive mechanism comprises: a magnetic arrangement operably coupled with the reflector, and an electromagnet operable to magnetically interact with the magnetic arrangement to move (e.g., oscillate) the reflector at a resonant frequency. The magnetic arrangement may include one or more magnets attached directly or indirectly to the reflector. The electromagnet may include one or more coils.

Optionally, the light beam scanner further comprises a frame to which the reflector is connected and a reflector support structure to which the frame is connected and which includes a space receiving the resonance-based drive mechanism (e.g., the magnetic arrangement and the electromagnet).

Optionally, the frame is connected to the reflector support structure via one or more hinges. For example, the one or more hinges may be flexible hinge(s). For example, the one or more hinges may be torsional hinge(s). For example, the one or more hinges may be made of polymer (e.g., BoPET (bi-axially-oriented polyethylene terephthalate)).

Optionally, the galvanometer-based drive mechanism is operable to move the reflector support structure and the resonance-based drive mechanism to move the reflector relative to the optical assembly.

Optionally, the reflected light beam comprises a pulsed laser beam. The pulsed laser beam may consist of laser pulses with a single wavelength. Or the pulsed laser beam may comprise laser pulses with two, three, or more wavelengths.

Optionally, the reflector is arranged to reflect the photoacoustic signals from the object, e.g., to the transducer unit.

Optionally, the reflector comprises a mirror with a metallic material layer. The metallic material may include aluminium. The metallic material layer may be an aluminium layer.

Optionally, the reflector and the resonance-based drive mechanism are provided by a resonant mirror (e.g., single-axis resonant scanning mirror, multi-axis resonant scanning mirror, etc.).

Optionally, the handheld device further comprises an acoustic collimator operable to collimate acoustic signals (including the photoacoustic signals). The acoustic collimator may include an acoustic lens, e.g., an optically-transparent acoustic lens.

Optionally, the light beam is a first light beam, and the optical assembly is arranged to manipulate a second light beam received from a light source to provide the first light beam.

Optionally, the optical assembly is arranged to focus or converge the second light beam such that the first light beam is a converging light beam.

Optionally, the optical assembly comprises an optical collimator and a lens assembly. The optical collimator and the lens assembly may be optically aligned. Optionally, the lens assembly comprises an optical objective lens and an optical correction lens, which may be optically aligned. The optical correction lens may include an achromatic lens.

Optionally, the optical assembly further comprises an optical connector or coupler for connecting with an optical fiber arranged to couple the light source with the optical assembly. The connector may be in the form of a port, a socket, a plug, etc.

Optionally, the optical assembly further comprises an optical-acoustic combiner arranged to reflect light beam to the reflector, e.g., to provide the first light beam to the reflector.

Optionally, the optical-acoustic combiner is acoustically-transparent to allow photoacoustic signals to pass.

Optionally, the optical-acoustic combiner is arranged to merge the light beam and the photoacoustic signals coaxially.

Optionally, the optical-acoustic combiner comprises a first prism, and second prism, and an acoustically-transparent optical-reflective material arranged between the two prisms. The first and second prisms may be right-angled or isosceles triangular prisms. The acoustically-transparent optical-reflective material may be solid or liquid. In one example, the acoustically-transparent optical-reflective material comprises aluminium.

Optionally, the reflector, the optical-acoustic combiner, and the transducer unit are arranged such that the photoacoustic signals from the object are arranged to reach the transducer unit via the reflector and the optical-acoustic combiner.

Optionally, the transducer unit includes one or more transducer elements (e.g., one or more piezoelectric transducer elements). Optionally, the transducer unit includes a transducer array formed by multiple transducer elements. The transducer array may be a 1D array (e.g., linear array, curved array, phased array) or a 2D array. In some embodiments, the transducer unit may selectively transmit and receive acoustic (e.g., ultrasound) signals. In some embodiments, the transducer unit is only operated to receive acoustic/photoacoustic (e.g., ultrasound) signals.

Optionally, the handheld device comprises a body with a handle portion and a head portion. The light beam scanner, the transducer unit, and at least part of the optical assembly may be arranged in the head portion.

Optionally, the handheld device is in the form of a probe. The handle portion may be elongated. The handle portion may be straight.

Optionally, the head portion includes a chamber for receiving an acoustic coupling medium. At least the reflector and the transducer unit are arranged in the chamber and are arranged to be immersed in the acoustic coupling medium during operation of the device. The acoustic coupling medium may include an acoustic coupling fluid, such as liquid (e.g., water, oil, etc.). The handheld device may further include one or more inlet(s) and one or more outlet(s) for the chamber. Inlet and outlet may be provided by the same opening or different openings.

Optionally, the handle portion is hollow, e.g., for receiving an optical fiber arranged to couple a light source with the optical assembly. The handle portion may additionally or alternatively receive power and/or data wires, cables, etc.

Optionally, the head portion includes an imaging window for allowing the photoacoustic signals and the reflected light beam to pass. The imaging window may be acoustically-and-optically-transparent or translucent.

Optionally the handheld device further comprises the light source.

Optionally the handheld device further comprises a controller for controlling operation of the first and/or second drive mechanisms.

Optionally, the handheld device further comprises an amplifier unit operably connected with the transducer unit. The amplifier unit may include one or more amplifiers arranged between the transducer unit and the data acquisition unit to amplify the signals generated by the transducer unit. In some embodiments, each of the transducer elements in the transducer unit is associated with a respective amplifier.

Optionally, the handheld device further comprises a data acquisition unit connected with the transducer unit for processing signals generated by the transducer unit as a result of the transducer unit receiving the photoacoustic signals. The data acquisition unit may include one or more channels for connecting with the transducer unit. In some embodiments each channel is for a respective transducer element in the transducer unit.

Optionally, the handheld device further comprises a controller for controlling operation of the first and/or second drive mechanisms.

Optionally, the handheld device further comprises a data processor for data processing system for processing signals generated by the transducer unit as a result of the transducer unit receiving the photoacoustic signals, to generate photoacoustic-based images (structural (e.g., anatomical) or functional (e.g., sO2, flow speed) photoacoustic images) of the object.

In a second aspect, there is provided a photoacoustic microscopy system that includes the handheld device of the first aspect. For example, the photoacoustic microscopy system may be used for optical-resolution photoacoustic microscopy. For example, the photoacoustic microscopy system may be used for intraoperative photoacoustic microscopy. For example, the photoacoustic microscopy system may be used for structural and/or functional photoacoustic microscopy of an object. For example, the photoacoustic microscopy system may be used for one or more of: in vivo photoacoustic microscopy, ex vivo photoacoustic microscopy, in vitro photoacoustic microscopy, etc. The object may be an animal, a human, a phantom, a tissue sample, etc.

Optionally, the photoacoustic microscopy system is portable, movable (e.g., wheeled), etc.

Optionally, the photoacoustic microscopy system further includes a light source optically coupled with the handheld device. The light source may include or consist of a laser source. The laser source may be arranged to provide pulsed laser beam with one, two, three, or more wavelengths (e.g., isosbestic wavelength(s) and/or non-isosbestic wavelength(s)). Example wavelength includes 532 nm, 545 nm, and 558 nm. The laser source may include one or more laser generators each arranged to generate laser pulses. The laser generators may generate laser pulses of different wavelengths. The light source, or the laser source, may consist of a single laser generator. The laser source may further include one or more laser manipulation assemblies for manipulating the laser pulses to form the pulsed laser beam. Each laser manipulation assembly may include one or more of: beam splitter, polarization adjuster, optical coupler, single mode optical fiber (Raman), optical combiner (dichroic mirror), etc. In some embodiments, the one or more laser manipulation assemblies can be arranged to provide pulsed laser beam with multiple wavelengths based on pulsed laser signal of single wavelength from the laser generator.

Optionally, the photoacoustic microscopy system further includes an optical fiber coupling the light source with the handheld device to provide pulsed laser beam from the light source to the handheld device. The optical fiber may be a single-mode optical fiber.

Optionally, the photoacoustic microscopy system further includes a controller for controlling operation of the first drive mechanism and the second drive mechanism. The controller may include a first control portion for controlling operation of the first drive mechanism and a second control portion for controlling operation of the second drive mechanism. The controller may be implemented using suitable hardware and software. In one example, the controller may include a field programmable gate array or a field programmable gate array card.

Optionally, the photoacoustic microscopy system further includes a data acquisition unit connected with the transducer unit for processing signals generated by the transducer unit as a result of the transducer unit receiving the photoacoustic signals. The data acquisition unit may include one or more channels for connecting with the transducer unit. In some embodiments each channel is for a respective transducer element in the transducer unit.

Optionally, the photoacoustic microscopy system further includes an amplifier unit. The amplifier unit may include one or more amplifiers arranged between the transducer unit and the data acquisition unit to amplify the signals generated by the transducer unit. In some embodiments, each of the transducer elements in the transducer unit is associated with a respective amplifier.

Optionally, the photoacoustic microscopy system is operable in, at least, a first mode, in which the photoacoustic microscopy system is operated to image the same part of the object without moving the handheld device relative to the object, and a second mode, in which the photoacoustic microscopy system is operated to image different parts of the object with the handheld device moved relative to the object. The first mode may be referred to as a video-camera mode. The second mode may be referred to as a simultaneous localization and mapping mode.

Optionally, the photoacoustic microscopy system further comprises a data processing system for processing signals generated by the transducer unit as a result of the transducer unit receiving the photoacoustic signals, to generate photoacoustic-based images of the object. The photoacoustic-based images may be structural (e.g., anatomical) or functional (e.g., sO2, flow speed) images produced based on the photoacoustic signals.

Optionally, the data processing system comprises one or more processors and memory storing one or more programs configured to be executed by the one or more processors, the one or more programs comprise instructions for: performing an image stitching operation to combine photoacoustic-based images of the object obtained in the second mode.

Optionally, the instructions for performing the image stitching operation comprises instructions for: extracting, based on a feature detection algorithm, features in a first photoacoustic-based image and features in a second photoacoustic-based image, wherein a field of view of the first photoacoustic-based image partly overlaps with a field of view of the second photoacoustic-based image, identifying features in the first photoacoustic-based image and features in the second photoacoustic-based image that correspond, determining a transform function for transforming one or both of the first and second photoacoustic-based images such that the first and second photoacoustic-based images can be registered and stitched, and registering and stitching the first and second photoacoustic-based images based on the determined transform function. The first and second photoacoustic-based images may be of the same size or different sizes. The first and second photoacoustic-based images may be structural (e.g., anatomical) or functional (e.g., sO2, flow speed) images produced based on the photoacoustic signals.

Optionally, the feature detection algorithm comprises a scale-invariant feature transform (SIFT) algorithm, a speeded-up robust features (SURF) algorithm, etc.

Optionally, the transform function is an affine transform function.

Optionally, the instructions for performing the image stitching operation further comprises instructions for: detecting outlier features from the extracted features in the first photoacoustic-based image and/or extracted features in the second photoacoustic-based image, and removing or ignoring the outlier features such that the outlier features are not processed in the identifying of features that correspond.

Optionally, the detecting of the outlier features is based on a random sample consensus method.

Optionally, the one or more programs further comprise instructions for: performing a compensation operation prior to performing the image stitching operation. The compensation operation may include one or more of: a scan trajectory distortion compensation operation to account for movement of the handheld device relative to the object in the second mode, a first scan axis distortion compensation operation to account for distortion in the first scan axis, a second scan axis distortion compensation operation to account for distortion in the second scan axis, etc.

In a third aspect, there is provided a data processing system for processing photoacoustic-based images (structural (e.g., anatomical) or functional (e.g., sO2, flow speed) photoacoustic images) obtained from the system of the second aspect. The data processing system comprises one or more processors and memory storing one or more programs configured to be executed by the one or more processors, the one or more programs comprise instructions for: performing an image stitching operation to combine photoacoustic-based images of the object obtained in the second mode.

Optionally, the instructions for performing the image stitching operation comprises instructions for: extracting, based on a feature detection algorithm, features in a first photoacoustic-based image and features in a second photoacoustic-based image, wherein a field of view of the first photoacoustic-based image partly overlaps with a field of view of the second photoacoustic-based image, identifying features in the first photoacoustic-based image and features in the second photoacoustic-based image that correspond, determining a transform function for transforming one or both of the first and second photoacoustic-based images such that the first and second photoacoustic-based images can be registered and stitched, and registering and stitching the first and second photoacoustic-based images based on the determined transform function.

Optionally, the feature detection algorithm comprises a scale-invariant feature transform (SIFT) algorithm, a speeded-up robust features (SURF) algorithm, etc.

Optionally, the transform function is an affine transform function.

Optionally, the instructions for performing the image stitching operation further comprises instructions for: detecting outlier features from the extracted features in the first photoacoustic-based image and/or extracted features in the second photoacoustic-based image; and removing or ignoring the outlier features such that the outlier features are not processed in the identifying of features that correspond.

Optionally, the detecting of the outlier features is based on a random sample consensus method.

Optionally, the one or more programs further comprise instructions for: performing a compensation operation prior to performing the image stitching operation. The compensation operation may include one or more of: a scan trajectory distortion compensation operation to account for movement of the handheld device relative to the object in the second mode, a first scan axis distortion compensation operation to account for distortion in the first scan axis, a second scan axis distortion compensation operation to account for distortion in the second scan axis, etc.

In a fourth aspect, there is provided a method for processing photoacoustic-based images (structural (e.g., anatomical) or functional (e.g., sO2, flow speed) photoacoustic images). The method includes performing an image stitching operation to combine photoacoustic-based images with overlapping field of view. The image stitching operation includes: extracting, based on a feature detection algorithm, features in a first photoacoustic-based image and features in a second photoacoustic-based image, wherein a field of view of the first photoacoustic-based image partly overlaps with a field of view of the second photoacoustic-based image, identifying features in the first photoacoustic-based image and features in the second photoacoustic-based image that correspond, determining a transform function for transforming one or both of the first and second photoacoustic-based images such that the first and second photoacoustic-based images can be registered and stitched, and registering and stitching the first and second photoacoustic-based images based on the determined transform function.

Optionally, the feature detection algorithm comprises a scale-invariant feature transform (SIFT) algorithm, a speeded-up robust features (SURF) algorithm, etc.

Optionally, the transform function is an affine transform function.

Optionally, the method further comprises: detecting outlier features from the extracted features in the first photoacoustic-based image and/or extracted features in the second photoacoustic-based image; and removing or ignoring the outlier features such that the outlier features are not processed in the identifying of features that correspond.

Optionally, the detecting of the outlier features is based on a random sample consensus method.

Optionally, the method further comprises: performing a compensation operation prior to performing the image stitching operation. The compensation operation may include one or more of: a scan trajectory distortion compensation operation, a first scan axis distortion compensation operation, a second scan axis distortion compensation operation, etc.

In a fifth aspect, there is provided a computer program comprising instructions which, when the computer program is executed by a computer, cause or facilitate the computer to carry out the method of the fourth aspect.

In a sixth aspect, there is provided a non-transitory computer-readable storage medium storing one or more programs configured to be executed by one or more processors, the one or more programs including instructions for carrying out the method of the fourth aspect.

Other features and aspects of the invention will become apparent by consideration of the detailed description and accompanying drawings. Any feature(s) described herein in relation to one aspect or embodiment may be combined with any other feature(s) described herein in relation to any other aspect or embodiment as appropriate and applicable.

Terms of degree such that "generally", "about", "substantially", or the like, are, depending on context, used to take into account manufacture tolerance, degradation, trend, tendency, practical applications, etc. The term "optically-transparent" means optical signals or waves can pass through, with some (e.g., <25%, <20%, <15%, <10%, <5%, <2%, etc.) or without signal attenuation/loss, etc. The term "acoustically-transparent" means acoustic/photoacoustic signals or waves can pass through, with some (e.g., <25%, <20%, <15%, <10%, <5%, <2%, etc.) or without signal attenuation/loss, etc.

Unless otherwise specified, the terms "connected", "coupled", "mounted", or the like, are intended encompass both direct and indirect connection, coupling, mounting, etc.

BRIEF DESCRIPTION OF THE DRAWINGS

Embodiments of the invention will now be described, by way of example, with reference to the accompanying drawings in which.

DETAILED DESCRIPTION

Figure 1:
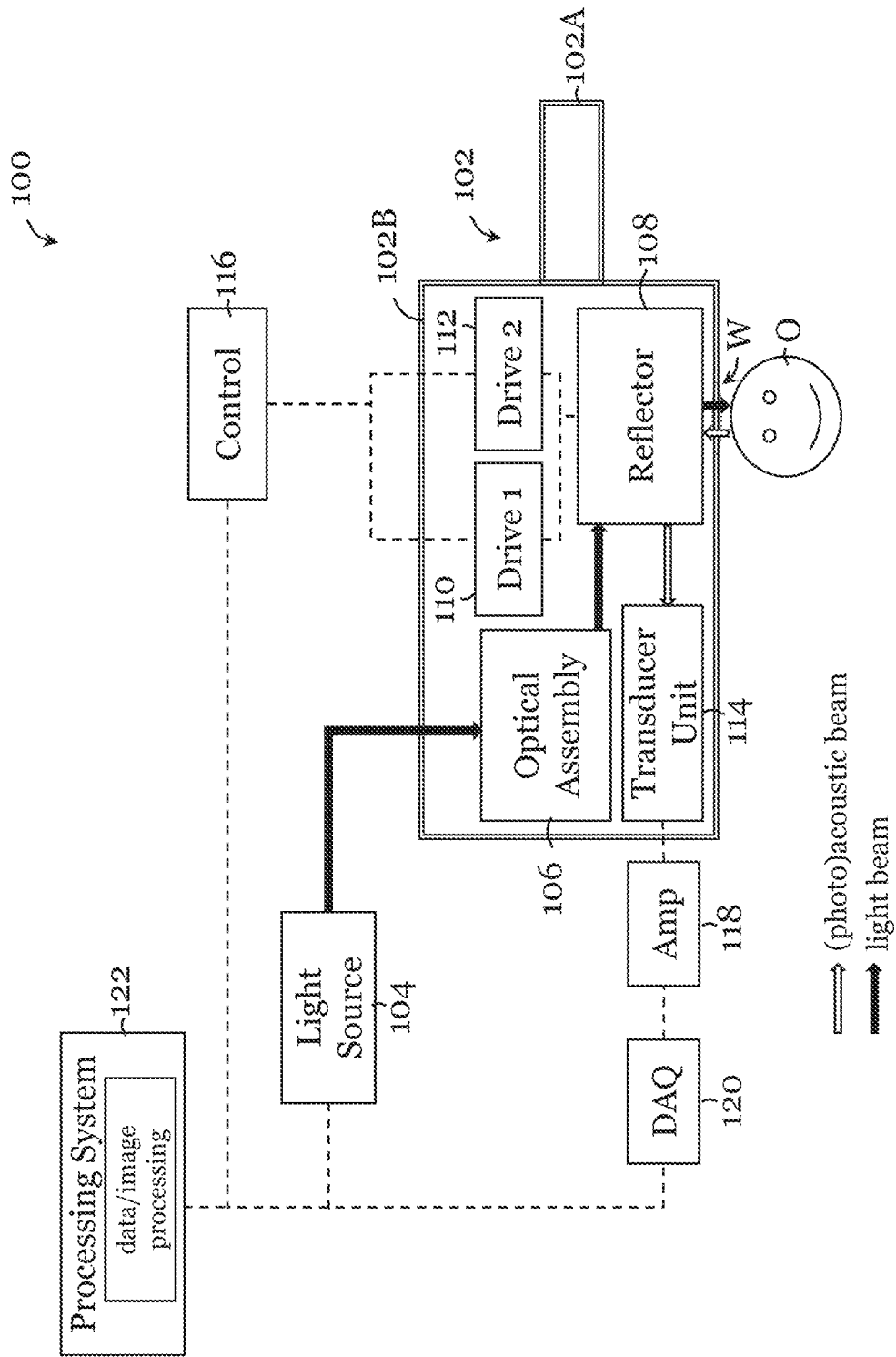
FIG. 1 is a schematic block diagram of a photoacoustic microscopy system with a handheld device for photoacoustic microscopy in one embodiment.

FIG. 1 schematically illustrates a photoacoustic microscopy system 100 in one embodiment. The system 100 may be used for structural and/or functional photoacoustic microscopy, intraoperative photoacoustic microscopy, etc. of an object O. The system 100 may be used for optical-resolution photoacoustic microscopy of an object O. The object O may be an animal, a human, a phantom, a tissue sample, etc.

The system 100 includes a handheld device 102, a light source 104 optically coupled with the handheld device 102, and various control and processing means for controlling operation of the device 102 and system 100.

Referring to FIG. 1, the handheld device 102 includes an optical assembly 106. The optical assembly 106 is arranged to provide a light beam to the reflector 108. In this embodiment, the optical assembly 106 is optically coupled with an external light source 104, optionally via an optical fiber, to receive a light beam from the light source 104. The optical assembly 106 is arranged to manipulate the received light beam and provide a manipulated light beam to the reflector 108. In one example, the optical assembly 106 is operable to focus or converge the received light beam such that the manipulated light beam is a converging light beam. The optical assembly 106 may include any combination of one or more lenses, prisms, and/or mirrors for manipulating the light beam. In one example, the optical assembly 106 includes an optical collimator and a lens assembly that may be optically aligned. The lens assembly may include, at least, an optical objective lens and an optical correction lens, which may be optically aligned. The optical correction lens may include an achromatic lens. In one example, the optical assembly 106 also includes an optical-acoustic combiner arranged to reflect light beam to the reflector 108. The optical-acoustic combiner may be acoustically-transparent to allow photoacoustic signals to pass. The optical-acoustic combiner may merge the light beam and the photoacoustic signals coaxially. The optical-acoustic combiner may be formed by two prisms and an acoustically-transparent optical-reflective material (solid or liquid) arranged between the two prisms. The two prisms may be right-angled or isosceles triangular prism, with the slanted face arranged in facing relationship. The optical assembly 106 may include an optical connector for connecting with the optical fiber that optically couples with the light source 104.

The handheld device 102 also includes a light beam scanner with the reflector 108 and two drive mechanisms 110, 112 for moving the reflector 108 to provide a scanning light beam to the object O. The handheld device 102 may facilitate freehand photoacoustic microscopy.

The reflector 108 is arranged to reflect the light beam from the optical assembly 106 to provide a reflected light beam (e.g., pulsed laser beam with one or more wavelengths) to the object O for photoacoustic imaging. The reflector 108 may be any device capable of deflecting propagation light signals and optionally acoustic signals. The reflector 108 may include a metal or dielectric mirror (planar or curved), prism, lens, or any combination thereof. In one example, the reflector 108 is also arranged to reflect the photoacoustic signals received from the object O (photoacoustic signals generated by the object O as a result of irradiating the object O with the light beam).

The two drive mechanisms 110, 112 are each operable to move (e.g., rotate, translate, etc.) the reflector 108 relative to the optical assembly 106, to move the reflected light beam (as reflected by the reflector 108) relative to the object O for scanning the object O. In one example, the two drive mechanisms 110, 112 are different types of drive mechanisms. Example types of drive mechanism include MEMS based drive mechanism, galvanometer based drive mechanism, resonance (e.g., voice coil) based drive mechanism, piezoelectric based drive mechanism, solid state based drive mechanism, etc. The two drive mechanisms 110, 112 may be operable independently, either separately (one at a time) or simultaneously. In one embodiment, the first drive mechanism 110 is operable to rotate or oscillate the reflector 108 about a first axis, e.g., to move the reflected light beam relative to the object O along a first scan axis, and the second drive mechanism 112 is operable to rotate or oscillate the reflector 108 about a second axis, e.g., to move the reflected light beam relative to the object O along a second scan axis. The first axis is different from the second axis and the first scan axis is different from the second scan axis. The first and second axes may be arranged at an angle (e.g., about 90 degrees). The first and second scan axes may be arranged at an angle (e.g., about 90 degrees). In one example, the two drive mechanisms 110, 112 are arranged or controlled to move the reflector 108 at different rates, to move the reflector to provide different scanning ranges (along the first and second scan axes), to move the reflector to provide different scanning step sizes (along the first and second scan axes), etc. The scanning ranges may be in the order of millimeters, such as several or tens of millimeters. The scanning step sizes may be in the order of micrometers, such as several or tens of micrometers. In one example, the two drive mechanisms 110, 112 include a galvanometer-based drive mechanism and a resonance-based drive mechanism. The galvanometer-based drive mechanism may include a galvanometer-based motor. The resonance-based drive mechanism may include a magnetic arrangement operably coupled with the reflector 108, and an electromagnet operable to magnetically interact with the magnetic arrangement to move (e.g., oscillate) the reflector 108 at a resonant frequency. In one example, the light beam scanner further includes a frame supporting the reflector 108 and a reflector support structure which supports the frame and defines a space receiving the resonance-based drive mechanism. The frame mounted with the reflector 108 may be connected to the reflector support structure via one or more hinges, e.g., flexible hinge(s) or torsional hinge(s) made of polymer material(s) (e.g., BoPET (bi-axially-oriented polyethylene terephthalate)). In one example, the galvanometer-based drive mechanism can move the reflector support structure and hence the resonance-based drive mechanism received in the reflector support structure. In one example, the reflector 108 and the resonance-based drive mechanism are provided by a resonant mirror (e.g., single-axis resonant scanning mirror, multi-axis resonant scanning mirror, etc.).

The handheld device 102 also includes a transducer unit 114. The transducer unit 114 is arranged to detect photoacoustic signals emitted or otherwise provided by the object in response to receiving the reflected light beam. The transducer unit 114 can include any number of transducer elements, e.g., piezoelectric transducer elements. In one example, the transducer unit 114 includes a transducer array (1D or 2D; linear, curved, or phased array) formed by multiple transducer elements. In this example the transducer unit 114 is used to receive photoacoustic signals for photoacoustic imaging. In some other examples, the transducer unit 114 may additionally be used to transmit acoustic signals.

The handheld device 102 may additionally include an acoustic collimator operable to collimate acoustic signals (including the photoacoustic signals). The acoustic collimator may include an acoustic lens, which may be optically-transparent.

The handheld device 102 may be shaped like a probe. The handheld device 102 may include a body with a handle portion 102A, which may be elongated or straight, and a head portion 102B. The light beam scanner, the transducer unit, and at least part of the optical assembly 106 may be arranged in the head portion 102B. In one example, the head portion 102B includes a chamber for receiving an acoustic coupling medium (acoustic coupling fluid, such as liquid (e.g., water, oil, etc.) and one or more openings to act as inlet/outlet of the chamber. At least the reflector 108 and the transducer unit 114 may be arranged in the chamber and to be immersed in the acoustic coupling medium during operation of the handheld device 102. The head portion 102B may have an imaging window W arranged between the reflector 108 and the object O for allowing photoacoustic signals and the reflected light beam to pass. The imaging window W may be acoustically-and-optically-transparent or translucent. The handle portion 102A may be hollow, e.g., for receiving the optical fiber arranged to couple the light source 104 with the optical assembly 106 and one or more power and/or data wires, cables, etc.

As mentioned, the light source 104 is optically coupled with the handheld device 102, e.g., via an optical fiber, to provide light beam or signals to the handheld device 102. The light source may include a laser source arranged to provide pulsed laser beam with one, two, three, or more wavelengths (e.g., isosbestic wavelength(s) and/or non-isosbestic wavelength(s)). Example wavelength includes 532 nm, 545 nm, and 558 nm. The laser source may include one or more laser generators each arranged to generate laser pulses of one or more, the same or different, wavelengths, and one or more laser manipulation assemblies for manipulating the laser pulses to form the pulsed laser beam. In one example, the laser source includes only one laser generator. Each laser manipulation assembly may include one or more of: beam splitter, polarization adjuster, optical coupler, single mode optical fiber (Raman), optical combiner (dichroic mirror), etc. In one example, the one or more laser manipulation assemblies can provide pulsed laser beam with multiple wavelengths based on pulsed laser signal of a single wavelength from the laser generator. The optical fiber that optically couples the light source 104 with the handheld device 102 may be a single-mode optical fiber. Some other examples of the laser source can be found in the US patent application with application Ser. No. 15/493,283 and entitled "System and method for providing multi-wavelength laser for fast functional photoacoustic microscopy" and US patent application with application Ser. No. 16/926,965 and entitled "Determining flow speed based on photoacoustic imaging and sensing", the entire contents of these two US patent applications are hereby incorporated by reference to the present disclosure.

Referring to FIG. 1, the system 100 further includes a controller 116 for controlling operation of the two drive mechanisms 110, 112. The controller 116 may be implemented using suitable hardware and software, such as a field programmable gate array or a field programmable gate array card. The controller 116 may include two control portions, one for controlling one of the two drive mechanisms 110, 112 and another for controlling another one of the two drive mechanisms 110, 112. In one example, the controller 116 may be used for other control function, such as controlling the light source 104, the data acquisition unit 120, etc.

The system 100 further includes an amplifier unit 118 and a data acquisition unit 120 connected with the transducer unit 114 for processing signals generated by the transducer unit 114 as a result of the transducer unit receiving the photoacoustic signals. The amplifier unit 118 may include one or more amplifiers arranged between the transducer unit 114 and the data acquisition unit 120 to amplify the signals generated by the transducer unit 114. In one example, each transducer element in the transducer unit 114 is associated with a respective amplifier. The data acquisition unit 120 may include one or more channels for connecting with respective transducer element(s) in the transducer unit 114. The data acquisition unit 120 may be implemented using suitable hardware and software, such as a data acquisition card. In one example, the data acquisition unit 120 may be controlled by the controller 116.

The system 100 further includes a processing system 122. The processing system 122 may be arranged for processing signals generated by the transducer unit 114 as a result of the transducer unit 114 receiving the photoacoustic signals, to generate photoacoustic-based images of the object. The photoacoustic-based images may be structural (e.g., anatomical) or functional (e.g., sO2, flow speed) images produced based on the photoacoustic signals. The processing system 122 may include one or more processors and memory, for performing data and/or image processing operations.

In this embodiment, the system 100 is operable in multiple modes. In one mode, the system 100 is arranged to image the same part of the object O without moving the handheld device 102 relative to the object O. In another mode, the system 100 is arranged to image different parts of the object O with the handheld device 102 moved relative to the object O.

A skilled person appreciates that the system 100 may include additional comments not specifically illustrated. A skilled person also appreciates that various modifications can be made to the system 100 to provide other embodiments of the invention. For example, one or more components illustrated as external to the handheld device 102 may be incorporated into the handheld device 102. For example, the photoacoustic signals may be received by the transducer unit 114 directly (not via the reflector 108). The reflector 108 may be driven by additional drive mechanism(s). For example, the handheld device 102 can have a different form, shape, and/or structure, e.g., with more than one handle and/or more than one head portion, etc. The handheld device 102 may include internal power source (battery) or may be connected to an external power source (e.g., via power cable or inductively). For example, the controller 116 and the processing system 122 may be combined. For example, the controller 116 and the light source 104 may not be connected to the processing system 122.

Figure 2:
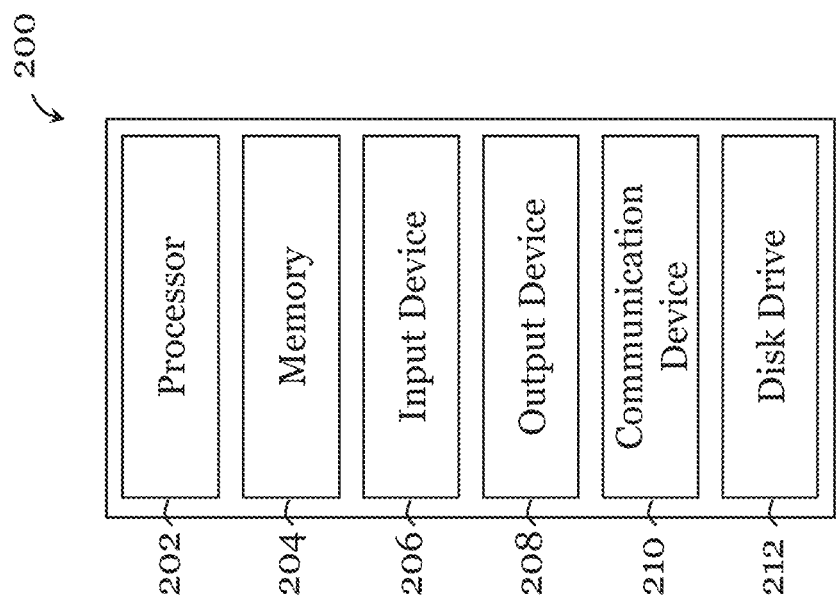
FIG. 2 is a block diagram of an information handling system operable as a data/image processing system in one embodiment.

FIG. 2 shows an example information handling system 200 that can operate as at least part of a controller (such as controller 116) or a data/image processing system (e.g., such as system 122) in one embodiment of the invention. The information handling system 200 generally comprises suitable components necessary to receive, store, and execute appropriate computer instructions, commands, or codes. The main components of the information handling system 200 are a processor 202 and a memory (storage) 204. The processor 202 may include one or more: CPU(s), MCU(s), logic circuit(s), Raspberry Pi chip(s), digital signal processor(s) (DSP), application-specific integrated circuit(s) (ASIC), field-programmable gate array(s) (FPGA), and/or any other digital or analog circuitry/circuitries configured to interpret and/or execute program instructions and/or to process signals and/or information and/or data. The memory 204 may include one or more volatile memory (such as RAM, DRAM, SRAM), one or more non-volatile memory (such as ROM, PROM, EPROM, EEPROM, FRAM, MRAM, FLASH, SSD, NAND, NVDIMM), or any of their combinations. Appropriate computer instructions, commands, codes, information and/or data may be stored in the memory 204. In one example, the memory may store one or more image/data processing programs with instructions for processing image data. Optionally, the information handling system 200 further includes one or more input devices 206. Examples of such input device 206 include: keyboard, mouse, stylus, image scanner, microphone, tactile/touch input device (e.g., touch sensitive screen), image/video input device (e.g., camera), etc. Optionally, the information handling system 200 further includes one or more output devices 208. Examples of such output device 208 include: display (e.g., monitor, screen, projector, etc.), speaker, disk drive, headphone, earphone, printer, additive manufacturing machine (e.g., 3D printer), etc. The display may include a LCD display, a LED/OLED display, or any other suitable display, which may or may not be touch sensitive. The display may be used to display photoacoustic-based images. The information handling system 200 may further include one or more disk drives 212 which may include one or more: solid state drive, hard disk drive, optical drive, flash drive, magnetic tape drive, etc. A suitable operating system may be installed in the information handling system 200, e.g., on the disk drive 212 or in the memory 204. The memory 204 and the disk drive 212 may be operated by the processor 202. Optionally, the information handling system 200 also includes a communication device 210 for establishing one or more communication links (not shown) with one or more other computing devices such as servers, personal computers, terminals, tablets, phones, watches, IoT devices, or other wireless or handheld computing devices. The communication device 210 may include one or more of: a modem, a Network Interface Card (NIC), an integrated network interface, a NFC transceiver, a ZigBee transceiver, a Wi-Fi transceiver, a Bluetooth® transceiver, a radio frequency transceiver, an optical port, an infrared port, a USB connection, or other wired or wireless communication interfaces. Transceiver may be implemented by one or more devices (integrated transmitter(s) and receiver(s), separate transmitter(s) and receiver(s), etc.). The communication link(s) may be wired or wireless for communicating commands, instructions, information and/or data. In one example, the processor 202, the memory 204, and optionally the input device(s) 206, the output device(s) 208, the communication device(s) 210 and the disk drive(s) 212 are connected with each other through a bus, a Peripheral Component Interconnect (PCI) such as PCI Express, a Universal Serial Bus (USB), an optical bus, or other like bus structure. In one embodiment, at least some of these components may be connected through a network such as the Internet or a cloud computing network. A person skilled in the art would appreciate that the information handling system 200 shown in FIG. 2 is merely exemplary and that the information handling system 200 can in other embodiments have different configurations (e.g., include additional components, has fewer components, etc.).

Figure 3:
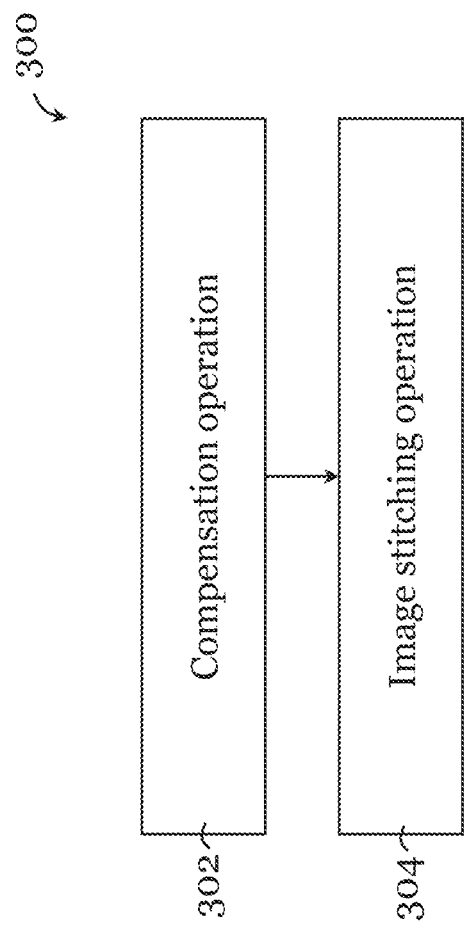
FIG. 3 is a method for processing photoacoustic-based images in one embodiment.

FIG. 3 is a method 300 for processing photoacoustic-based images in one embodiment. The method 300 may be used to process image data obtained using the system 100. The method 300 may be used to process photoacoustic-based images (structural (e.g., anatomical) or functional (e.g., sO2, flow speed) photoacoustic images), which may or may not be obtained using system 100. The method 300 may be performed using the system 100 or the system 200.

The method 300 includes, in step 302, performing a compensation operation. In one example, the compensation operation includes at least one of: a scan trajectory distortion compensation operation to account for movement of the handheld device 102 relative to the object in one operation mode of the system 100, a first scan axis distortion compensation operation to account for distortion in the first scan axis, and a second scan axis distortion compensation operation to account for distortion in the second scan axis.

The method 300 also includes, in step 304, performing an image stitching operation. The image stitching operation is arranged to combine photoacoustic-based images with overlapping field of view. In one example, the image stitching operation includes: (1) extracting, based on a feature detection algorithm, features in a first photoacoustic-based image and features in a second photoacoustic-based image, in which a field of view of the first photoacoustic-based image partly overlaps with a field of view of the second photoacoustic-based image; (2) identifying features in the first photoacoustic-based image and features in the second photoacoustic-based image that correspond; (3) determining a transform function for transforming one or both of the first and second photoacoustic-based images such that the first and second photoacoustic-based images can be registered and stitched; and (4) registering and stitching the first and second photoacoustic-based images based on the determined transform function. The feature detection algorithm may be a scale-invariant feature transform (SIFT) algorithm, a speeded-up robust features (SURF) algorithm, etc. The transform function may be an affine transform function. In one example, the image stitching operation includes: after extracting the features, detecting outlier features from the extracted features in the first photoacoustic-based image and/or extracted features in the second photoacoustic-based image. The detected outlier features are removed, discarded or otherwise not processed in subsequent identifying of features that correspond.

Figure 4:
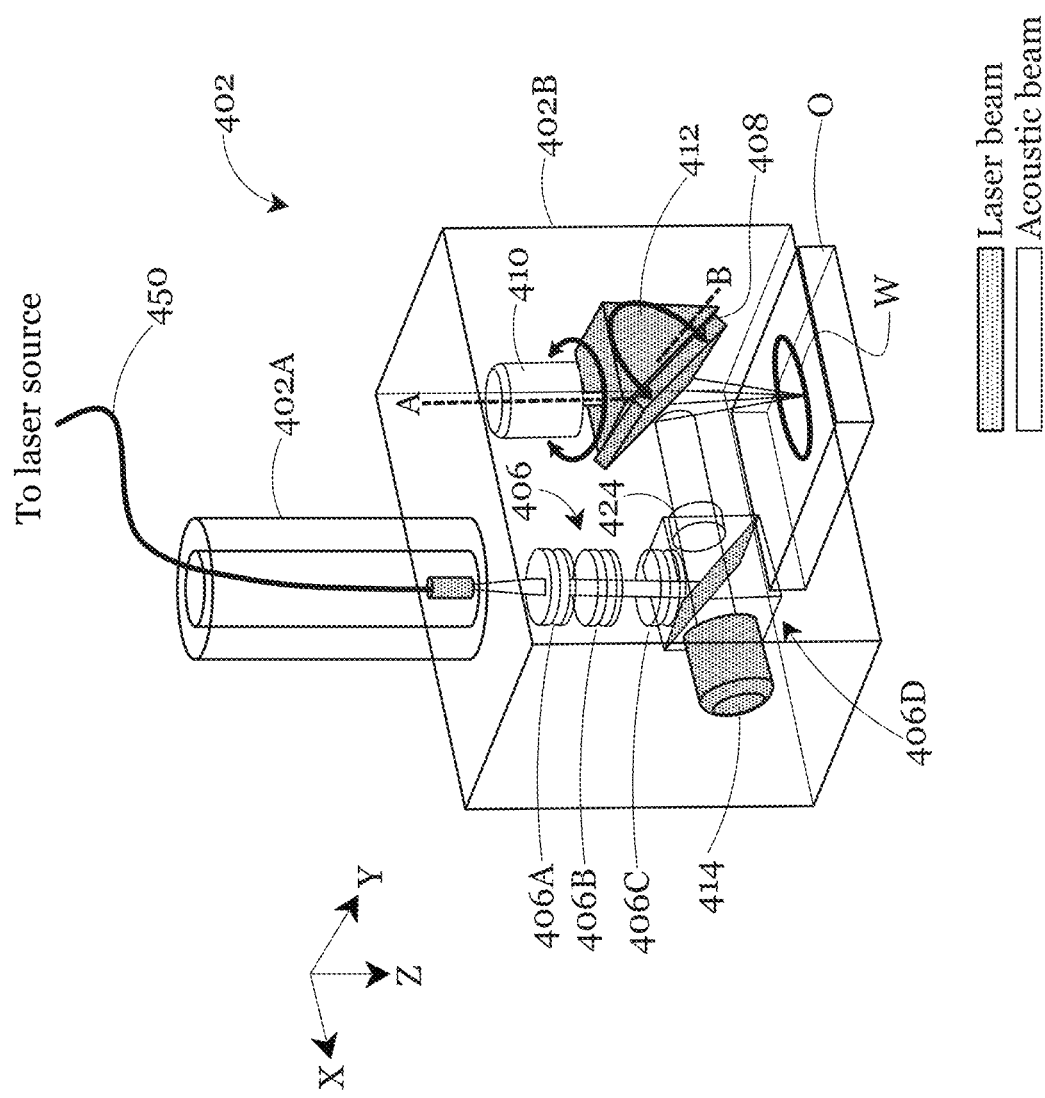
FIG. 4 is a schematic diagram of a handheld device for photoacoustic microscopy in one embodiment.

FIG. 4 shows a handheld device 402 for photoacoustic microscopy in one embodiment. The handheld device 402 is a more specific example of the handheld device 102 in FIG. 1 and so same/like components are annotated using the same reference plus "300" (i.e., component 104 generally corresponds to component 404). Some of the optical and electrical connections (e.g., wires, cables, etc.) are not shown in FIG. 4.

As shown in FIG. 4, the handheld device 402 includes a hollow handle portion 402A and a head portion 402B. In the head portion 402B, the handheld device 402 includes an optical assembly 406 with a set of optical lenses 406A-406C and an optical-acoustic beam combiner 406D, a hybrid resonant-galvo scanner, an acoustic lens 424, and an ultrasound transducer 414.

The optical assembly 406 is connected with a single-mode optical fiber 450 that runs through the hollow handle portion 402A and connects with a remote laser source, to receive laser beam from the laser source. In this example, the laser beam includes dual-wavelength (532 and 558 nm) nanosecond pulsed laser (up to 1-MHz pulse repetition rate) beam for photoacoustic excitation. The optical assembly 406 is arranged to manipulate the laser beam received from the laser source and provide a manipulated laser beam to the mirror 408. The optical lenses 406A-406C of the optical assembly 406 includes a collimator 406A for collimating the laser beam received from the laser source, as well as an objective lens 406B and a correction lens (e.g. achromatic lens) arranged to focus the laser beam and reduce optical aberration. The collimator and lens 406A-406C are optically aligned. The optical-acoustic beam combiner 406D, which is substantially acoustically transparent, includes two prisms with slanted faces in facing relationship and a layer of aluminum arranged between the two slanted faces to reflect the laser beam to the hybrid resonant-galvo scanner. The optical-acoustic beam combiner 406D is also optically aligned with the collimator and lens 406A-406C.

The hybrid resonant-galvo scanner has an aluminum-coated mirror 408 and two drive mechanisms 410, 412 for moving the mirror 408. One of the drive mechanism 410 is a galvanometer based motor, for controlling slow axis scanning. Another drive mechanism 412 is a resonant-based drive mechanism, for controlling fast axis scanning. The resonant-based drive mechanism 412 and the mirror 408 together can be referred to as a resonant mirror. The drive mechanism 410 is arranged to rotate the mirror 408 about a generally vertical axis A. The drive mechanism 412 is arranged to rotate the mirror 408 about a generally horizontal axis B. In this example, the aluminum-coated mirror is arranged to reflect about 95% laser light and about 90% acoustic waves. Laser beam from the optical assembly 406 is reflected by the mirror 408, through an imaging window W, to the object O for imaging. The drive mechanisms 410, 412 in the hybrid resonant-galvo scanner are arranged to move the mirror relative to the optical assembly 406, hence alter the travel direction of the laser beam reflected by the mirror 408, to "scan" the object O for imaging. The object O, in response to being irradiated with the laser beam, generates photoacoustic signals or waves. The induced photoacoustic waves are reflected by the mirror 408 and collimated by an acoustic lens 424. Then, the acoustic wave transmits through the optical-acoustic beam combiner 406D and is detected by an ultrasound transducer 414. In this example, the ultrasound transducer 414 is a piezo transducer that has a 50 MHz center frequency and a 78% bandwidth.

In this embodiment, the optical and acoustic foci are co-axially and confocally aligned by the device 402 to maximize the detection sensitivity. In this embodiment, the resonant mirror 408 scans the optical and acoustic beams together so that accurate alignment and high sensitivity are maintained. The hybrid resonant-galvo scanner with a mini-galvo scanner and a resonant mirror coupled to the mini-galvo scanner rotate the confocally aligned optical and acoustic beams in two scan directions for high-speed photoacoustic imaging (e.g., microscopy).

Figure 5:
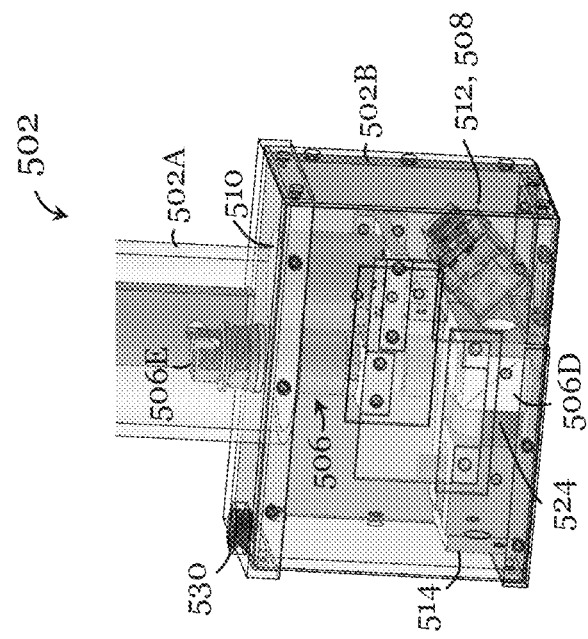
FIG. 5 is a schematic diagram of part of a handheld device for photoacoustic microscopy in one embodiment.

FIG. 5 illustrates part of a handheld device 502 for photoacoustic microscopy in one embodiment. The handheld device 500 has generally the same design as the device 402 and so same/like components are annotated using the same reference plus "100" (i.e., component 404 generally corresponds to component 504. Some of the optical and electrical connections (e.g., wires, cables, etc.) are not shown in FIG. 5.

As shown in FIG. 5, the handheld device 502 includes a hollow handle portion 502A and a head portion 502B. In the head portion 502B, the handheld device 502 includes an optical assembly 506 with a set of optical lenses and an optical-acoustic beam combiner 506D, a hybrid resonant-galvo scanner, an acoustic lens 524, and an ultrasound transducer 514. The hybrid resonant-galvo scanner includes a compact resonant mirror module and a miniature galvo scanner, which steers the optical and acoustic beams in two axes. The resonant mirror and the galvo scanner are independently driven to reduce or minimize interaction force between them. The optical assembly 506 may be arranged in a waterproof casing. The optical assembly 506 includes a connection interface 506E for connecting with an optical fiber or like optical means that couples with the laser source. The ultrasound transducer 514 may be arranged in a waterproof casing. The housing of the head portion 502B can be made with transparent or translucent materials.

The head portion 502B defines a chamber for containing (e.g., partly containing or completely filled with) an acoustic coupling medium and an opening 530 that can act as an inlet/outlet to the chamber. The acoustic coupling medium may include an acoustic coupling fluid, such as liquid (e.g., water, oil, etc.). At least the resonant mirror, the combiner 506D, the lens 524, and the transducer 514 may be immersed in the acoustic coupling medium during operation. The opening 530 may be closed or sealed by a door, seal, or the like.

Figure 6A:
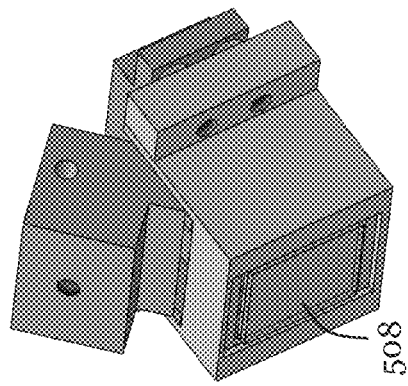
FIG. 6A is a schematic diagram of a resonator mirror module in the handheld device of FIG. 5.
Figure 6B:
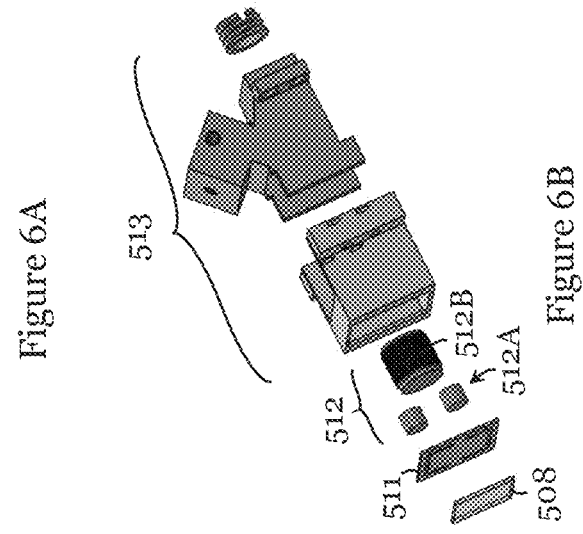
FIG. 6B is an exploded view of the resonator mirror module of FIG. 6A.

FIGS. 6A and 6B show the resonator mirror of the device 502. The resonant mirror includes reflector support structure 513, a resonant based drive mechanism 512 with a pair of magnets 512A and a driving coil 512B, a flexible-hinge frame 511 and an aluminum coated reflector 508. The reflector support structure 513 defines a space receiving the magnets 512A and coil 512B (electromagnet). The frame 511 is mounted to the reflector support structure 513 via one or more hinges. The reflector 508 is connected with the frame 511. In this example, the flexible-hinge frame 511 is fabricated from BoPET by laser cutting. The two magnets 512A are attached to the frame 511 hence reflector 508 using adhesives (e.g., glue). The coil 512B is controlled to generate a periodic magnetic field to drive the reflector 508 to oscillate at a resonant frequency for fast axis scanning. The resonator mirror of the device 502 is mounted to the shaft of a galvo motor for the slow axis scanning. Further details on BoPET hinges can be found, e.g., in Xu, S., Li, S. & Zou, J. *A micromachined water-immersible scanning mirror using BoPET hinges. Sensors Actuators, A Phys.* 298, 111564 (2019).

The resonant frequency of the resonant mirror can be determined as follows. The frequency of the resonant frequency in air $f_{air}$ can be calculated as $$f_{air} = \frac{1}{\pi}\sqrt{\frac{K}{J}}, \quad (1)$$

where J is the torsional moment $$J = wt^3\left[\frac{16}{3} - 3.36\frac{t}{w}\left(1 - \frac{t^4}{12w^4}\right)\right] \quad (2)$$

and K is the torsional stiffness of the BOPET hinge of the frame 511

$$K = \frac{G}{L}\left[tw^3\left\{\frac{1}{3} - 0.21\frac{w}{t}\left(1 - \frac{w^4}{w^4}\right)\right\}\right]. \quad (3)$$

G is the shear modulus, L, w, t are the length, width, and thickness of the BOPET hinge of the frame 511. In water, the resonant frequency decreased to $$f_{water} = f_{air}\sqrt{1 + \frac{3\pi\rho w_m}{2\rho_e t}\Gamma_t(k)}, \quad (4)$$

where ρ is the density of water, $\rho_e$ and $w_m$ are the effective density and width of the mirror-frame assembly, $\Gamma_t(k)$ is the normalized hydrodynamic load, and k is the mode number. In one example, the resonant frequency in water (as acoustic coupling medium) is 1288 Hz.

Figure 7:
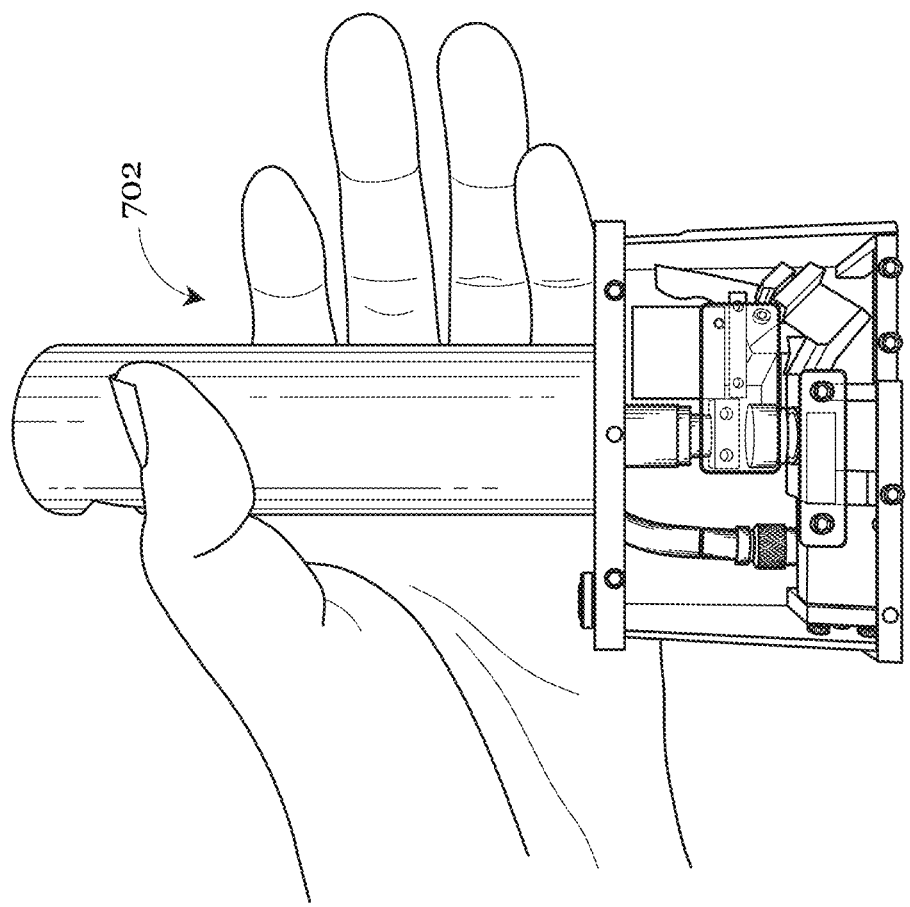
FIG. 7 is a picture of a fabricated handheld device for photoacoustic microscopy in one embodiment.

FIG. 7 shows a handheld probe 702 for photoacoustic microscopy fabricated in accordance with the designs of the devices 402 and 502. The size of the handheld probe 702 is 5.9×3.0×4.4 cm³, which is convenient for intraoperative imaging. In this example, the hybrid scanner of the handheld probe 702 has a scanning range of about 1.7 mm in the fast axis and about 5 mm in the slow axis. In this example, the aluminum-coated reflector has a length of 7 mm, a width of 6 mm, and a thickness of 0.4 mm. Each of the flexible hinges have a hinge length of 0.4 mm, a hinge width of 1.2 mm, a thickness of 0.3 mm, a shear modulus (G) of 0.02 GPa, and a density of 1.455 g/cm³. Each of the magnets is permanent magnet with a diameter of 2.5 mm, a height of 2 mm, and a density of 7.5 g/cm³. The driving coil has an inductance of 33 mH, a coil length of 4 mm, and a coil diameter of 3.5 mm.

Figure 8:
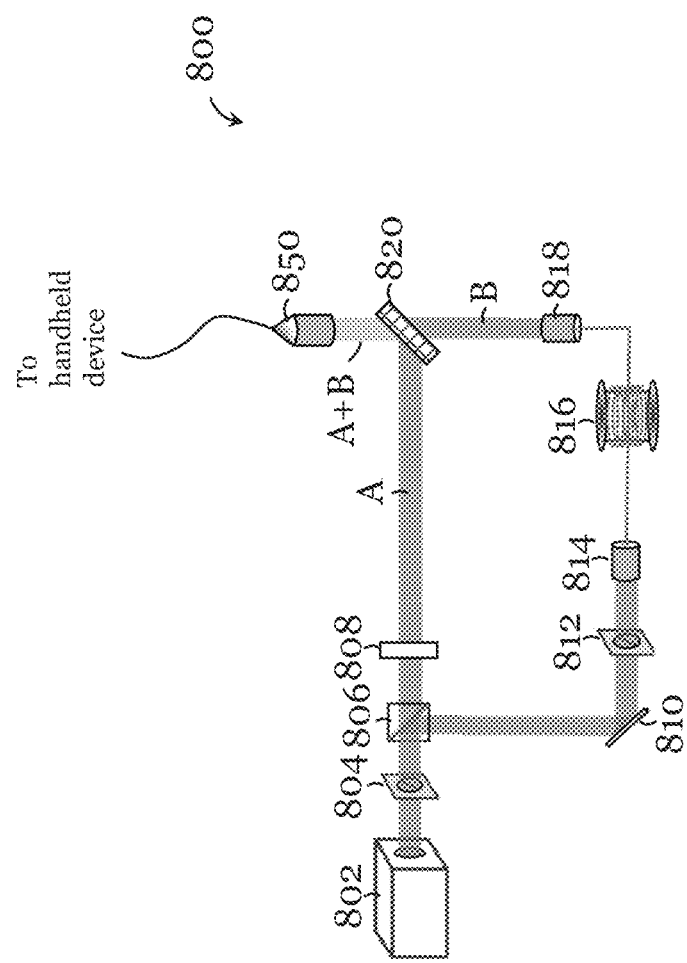
FIG. 8 is a schematic diagram of a light source for a photoacoustic microscopy system in one embodiment.

FIG. 8 illustrates a light source 800 for a photoacoustic microscopy system in one embodiment. The light source 800 may be used as the light source of the devices 102, 402, 502, 702, etc.

The light source 800 in this embodiment is a dual-wavelength pulsed laser source. The light source 800 includes a 532 nm pump laser 802 (VPFL-G-30, Spectra-Physics) arranged to generate provides 5 ns laser pulses (beam). The light source 800 also includes a half-wave plate 804 for adjusting polarization direction of the laser beam, and a polarization beam splitter for splitting the 532 nm laser beam into two, each with a respective optical path. In one of the optical path, the 532 nm beam is coupled into a 20 m polarization-maintaining single-mode fiber 816 (PMSM, HB450-SC, Fibercore) to generate a 558 nm wavelength via the stimulated Raman scattering (SRS) effect. In this example, the 20 m fiber also delays the laser beam by 100 ns. In this optical path, the 532 nm beam is reflected by a mirror 810, then passes through a half-wave plate 812 to improve or maximize the stimulated Raman scattering effect, the single-mode fiber 816 (via couplers 814, 818). In another one of the optical path, the 532 nm beam passes through a neural density filter. The two laser beams, the 558 nm and 532 nm beams, are merged via a dichroic mirror 820 (DM, T550lpxr-UF1, Chroma Technology Corp) and coupled into a 2 m polarization-maintaining single mode fiber via a coupler 850. In this example, the dichroic mirror 820 is a long pass dichroic mirror arranged to transmit the 558 nm beam and reflect the 532 nm beam. The polarization-maintaining single mode fiber can be connected with the system 100, the devices 402, 502, 702, etc.

One or more of the handheld devices 102, 402, 502, 702 may be used for freehand scanning/imaging, and the photoacoustic imaging system including it may operate in various operation modes. In one example, one of the operation modes is a video-camera mode. In the video-camera mode, the handheld device is used to image the object at a fixed position/location a high frame, to enable flexible real-time imaging. In another example, one of the operation modes is a simultaneous localization and mapping (SLAM) mode. In the SLAM mode, the handheld device is used to scan/image the object at different locations (i.e., the handheld device is moved relative to the object) and the data obtained can be processed using an image stitching algorithm to enlarge the field of view. Taking advantage of the handheld operation and high imaging speed, the probe can be used to scan along any trajectories relative to the object, breaking the field of view limit of conventional C-scan.

Figure 9:
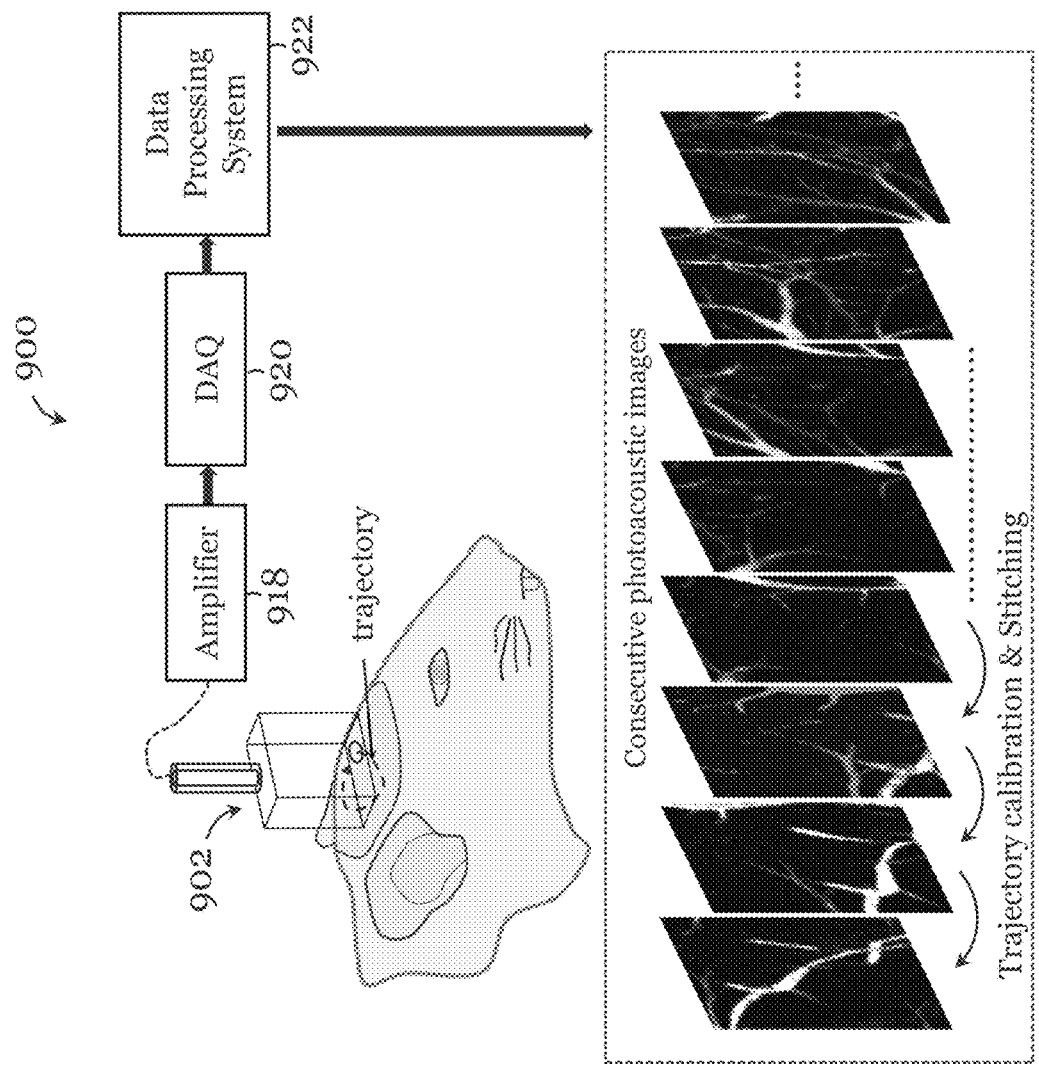
FIG. 9 is a schematic diagram of a photoacoustic microscopy system and its operation in one embodiment.

FIG. 9 illustrates a photoacoustic microscopy system 900 and its operation in SLAM mode in one embodiment. The system 900 is generally the same as the system 100. The scanning/imaging probe 902 may be the device 102, 502, 602, 702. The amplifier unit 918 may be the amplifier unit 118. The data acquisition unit 920 may be the data acquisition unit 120. The data processing system 922 may be the system 122, 200. In this example, the photoacoustic signals obtained from the object is amplified by the amplifier unit 918 with two 24 dB amplifiers (ZFL-500LN+, Mini-Circuits) and then digitized at 200 MHz by the data acquisition unit 920 with a data acquisition card (ATS9360, Alazar Technologies Inc). An FPGA card (PCIe-7852, National Instruments) is programmed to control the scanning and data acquisition operations.

As illustrated in FIG. 9, the object being imaged or scanned is a mouse. In the in SLAM mode, the scanning/imaging probe 902 move over the object along a trajectory to obtain series of photoacoustic images. The series of photoacoustic images are partially overlapped, which can be processed for trajectory calibration and stitching to expand the field of view. In one example of the SLAM Mode, a 5 Hz to 10 Hz C-scan rate can enable real-time imaging with minimal distortions with freehand scanning.

Figure 10:
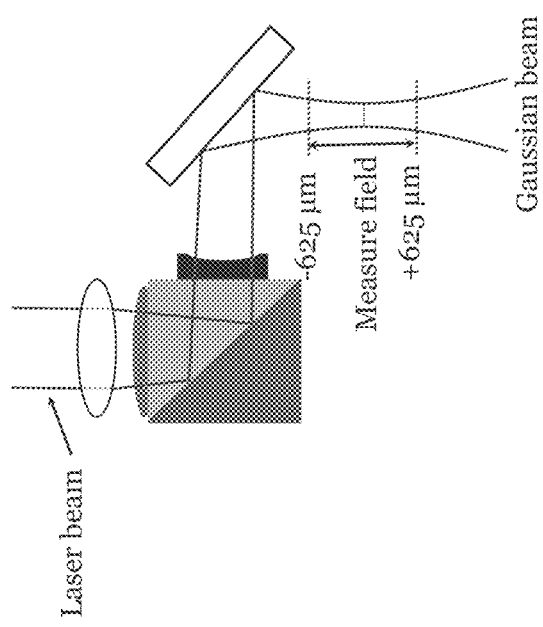
FIG. 10 is a schematic diagram of a laser beam in the handheld device for photoacoustic microscopy of FIG. 7 during operation and illustrating a depth of focus of the laser beam.
Figure 12:
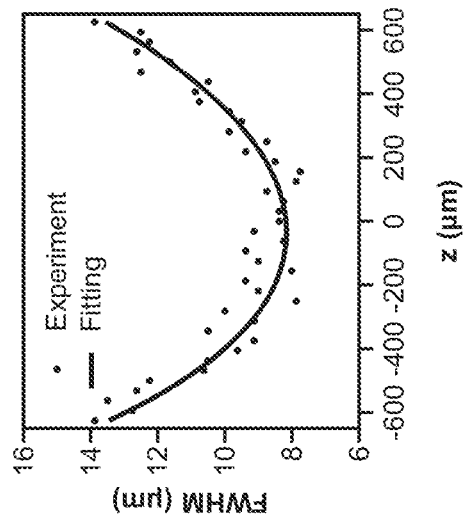
FIG. 12 is a graph showing lateral resolution of a 10-μm-diameter tungsten filament at different depths obtained in the resolution and penetration depth characterization experiment performed using the handheld device for photoacoustic microscopy of FIG. 7.
Figure 11:
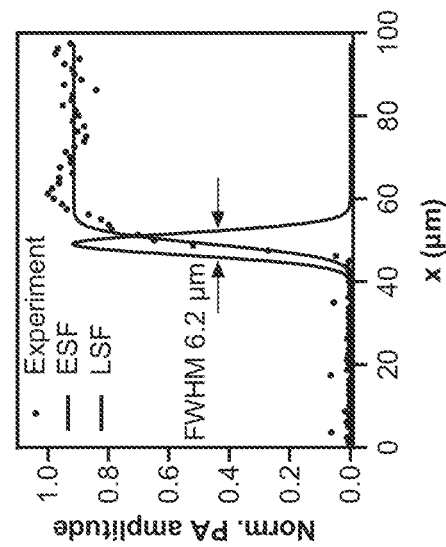
FIG. 11 is a graph showing lateral resolution in an optical focal plane obtained in a resolution and penetration depth characterization experiment performed using the handheld device for photoacoustic microscopy of FIG. 7 to image a stainless-steel sharp edge.
Figure 14:
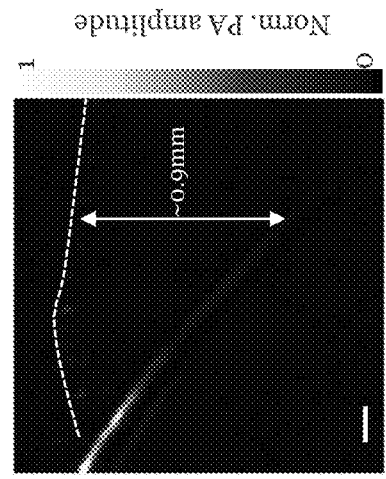
FIG. 14 is an image showing penetration depth of the tungsten filament obtained in the resolution and penetration depth characterization experiment performed using the handheld device for photoacoustic microscopy of FIG. 7 (the scale bar represents 200 μm)
Figure 13:
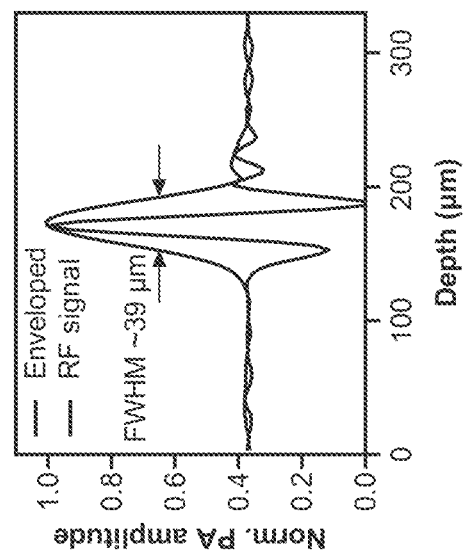
FIG. 13 is a graph showing axial resolution of the tungsten filament obtained in the resolution and penetration depth characterization experiment performed using the handheld device for photoacoustic microscopy of FIG. 7.

The resolution and imaging depth of the handheld probe 702 are characterized. FIG. 10 shows a laser beam provided to the object by the probe 702. The lateral resolution in a depth range of 1.25 mm is measured. The best resolution in the focal plane is measured using a stainless-steel sharp edge. A profile across the sharp edge is measured and fitted to an edge spread function (ESF), and the line spread function (LSF) is calculated. As shown in FIG. 11, the full width at half maximum (FWHM) of the LSF is about 6.2 µm. As shown in Supplementary FIG. 12, the FWHMs of a 10-µm-diameter tungsten filament is measured at different depths. In the 1.25-mm depth range, the lateral resolution is always finer than 14 µm. The axial resolution is also measured using the tungsten filament. As shown in Supplementary FIG. 13, a Hilbert-transformed A-line of the tungsten filament has an FWHM of 39 µm, which is close to the theoretical value of 34 µm (estimated with 1500-m/s sound speed and 39-MHz bandwidth). A human hair is inserted into the fresh chicken breast tissue to measure the penetration depth. The penetration depth with a signal-to-noise ratio of 6 dB is about 0.9 mm, as shown in FIG. 14.

As mentioned, image stitching operation may need to be performed on the images obtained using the device 102, 502, 602, 702, and associated system, e.g., in SLAM mode. In one example, the scanning trajectory is first calibrated to reduce image distortions. Then, the translation, rotation, and scaling between images are computed. Specifically the coordinates of the same features in two consecutive images are extracted using the scale-invariant feature transform (SIFT) and/or speeded-up robust features (SURF) methods. The feature points are used to determine an "affine" transformation matrix, which can transfer the two images to the same coordinates. By repeating this operation, stitch multiple partially overlapped images can be combined or stitched into a large image. The field of view of the stitched image is determined by the freehand-scanning, rather than one C-scan, and thus can be as large as needed. The following provide more detailed steps of image stitching and trajectory calibration in some examples.

Figure 15B:
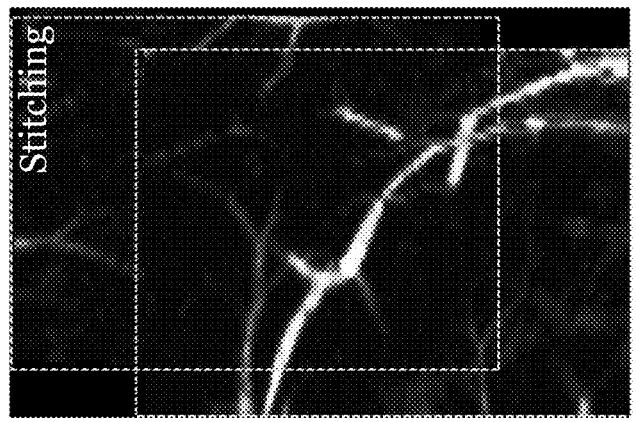
FIG. 15B illustrates a stitched or merged image formed from the two photoacoustic images of FIG. 15A.
Figure 15A:
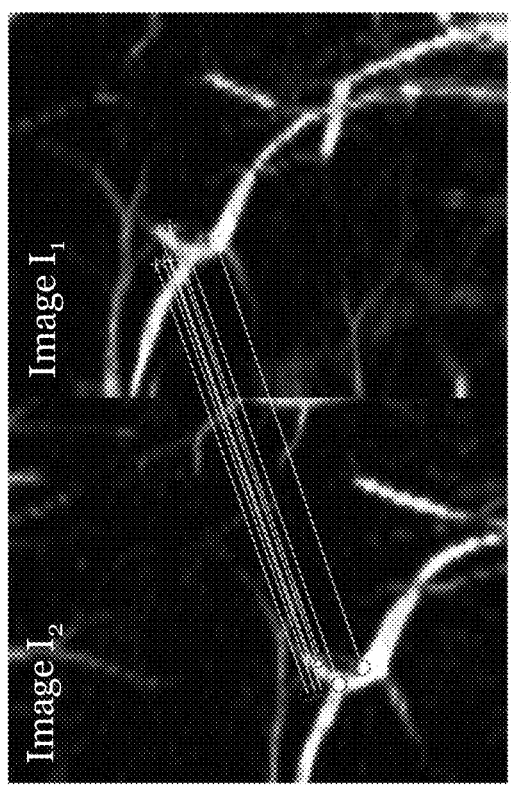
FIG. 15A illustrates two photoacoustic images with partly overlapped field of view for performing stitching operation.

In one example of image stitching, the image shift induced by freehand scanning can be expressed as "affine" deformation that includes translation, rotation, scaling, reflection, and shear mapping. Let I' be the image projection of 2D points I. I=[x, y] and I'=[x', y'] is the pixel coordinates from the image pair. Expand I' and I by adding 1 as the last element, i.e., I=[x, y, 1], and I'=[x', y', 1]. The affine transformation can be expressed as $$I'=MI \quad (5)$$

where M is a transformation matrix $$M = \begin{bmatrix} s \times \cos(\theta) & -s \times \sin(\theta) & t_x \\ s \times \sin(\theta) & s \times \cos(\theta) & t_y \\ 0 & 0 & 1 \end{bmatrix} \quad (6)$$

where s is the scaling parameter, θ is the rotation parameter, and $t_x$, $t_y$ are the translation parameters in the x and y-directions. The scale-invariant feature transform (SIFT) feature, speeded-up robust features (SURF), and "affine" transformation can be used to stitch the images. The process to stitch two images includes:

1. Extract feature points from image I1 and image I2 based on SIFT and/or SURF
2. Use random sample consensus (RANSAC) to remove outliers from the feature points and extract the incliners. Incliners I are from image $I_1$ and incliners I' are from image $I_2$ as shown in FIG. 15A (raw images obtained using device 702 and associated system)
3. The point pairs [I I'] is used to calculate the affine transform matrix "M" by least squares as $$M=(I^TI)^{-1}I^TI' \quad (7)$$

Determine s and θ. Let sc=s×cos(θ) and ss=s×sin(θ), the inverse of M can be obtained as $$M' = \begin{bmatrix} sc & -ss & 0 \\ ss & sc & 0 \\ t_x & t_y & 1 \end{bmatrix} \quad (8)$$

Figure 16A:
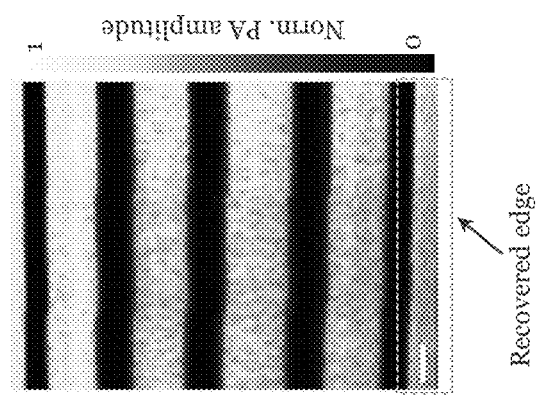
FIG. 16A shows a photoacoustic image of a stainless-steel grating obtained using the handheld device for photoacoustic microscopy of FIG. 7 without compensation for distortion in the fast scan axis (the scale bar represents 150 μm)
Figure 16B:
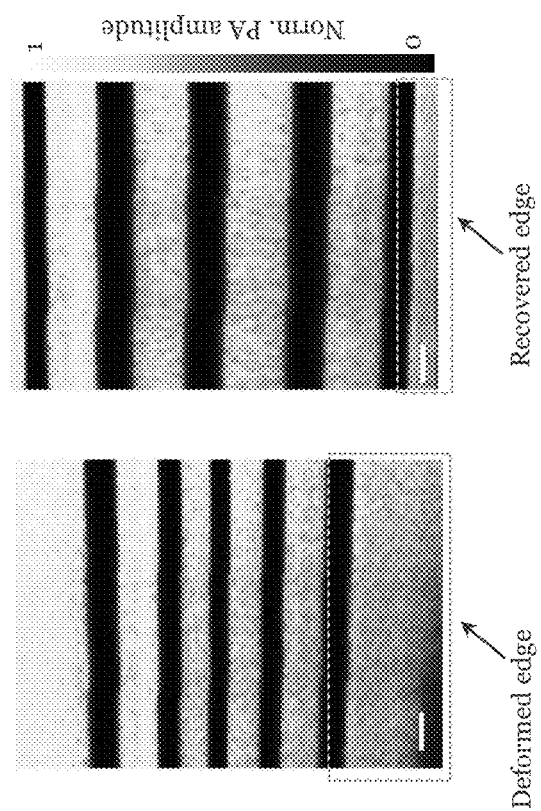
FIG. 16B shows a photoacoustic image of the stainless-steel grating obtained using the handheld device for photoacoustic microscopy of FIG. 7 with compensation for distortion in the fast scan axis (the scale bar represents 150 μm)
Figure 17A:
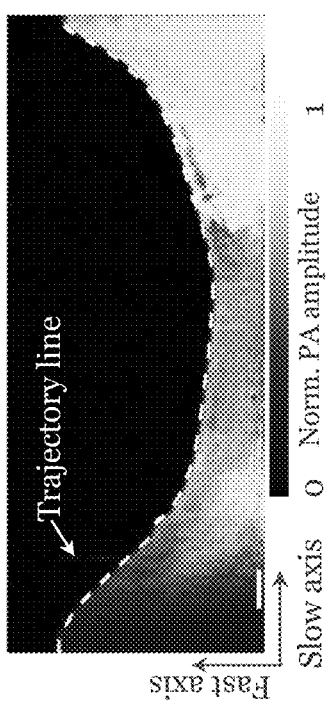
FIG. 17A shows a photoacoustic image of a straight edge blade obtained using the handheld device for photoacoustic microscopy of FIG. 7 with compensation for distortion in the fast scan axis and without compensation for trajectory distortion (the scale bar represents 320 μm)
Figure 17B:
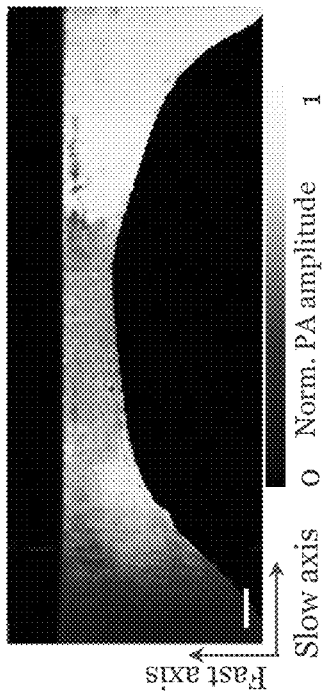
FIG. 17B shows a photoacoustic image of the straight edge blade obtained using the handheld device for photoacoustic microscopy of FIG. 7 with compensation for distortion in the fast scan axis and with compensation for trajectory distortion (the scale bar represents 320 μm)
Figure 17C:
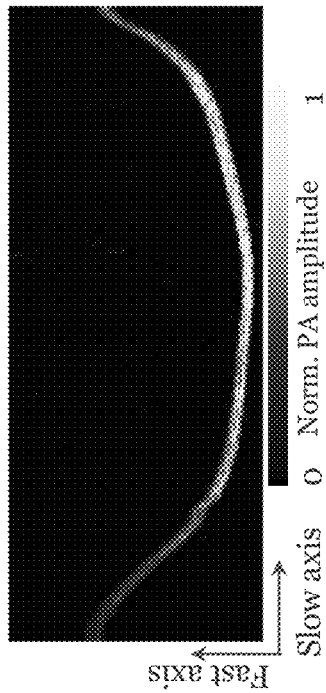
FIG. 17C shows a photoacoustic image of a straight human hair obtained using the handheld device for photoacoustic microscopy of FIG. 7 with compensation for distortion in the fast scan axis and without compensation for trajectory distortion (the scale bar represents 320 μm)
Figure 17D:
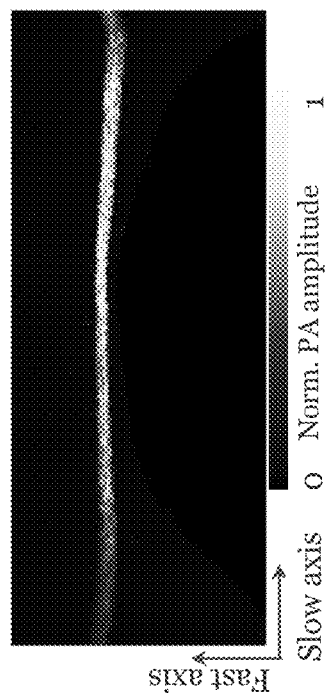
FIG. 17D shows a photoacoustic image of the straight human hair obtained using the handheld device for photoacoustic microscopy of FIG. 7 with compensation for distortion in the fast scan axis and with compensation for trajectory distortion (the scale bar represents 320 μm)
Figure 19B:
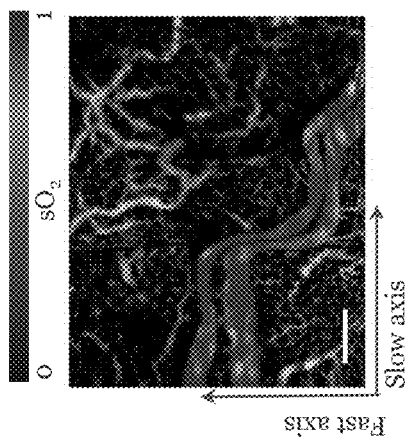
FIG. 19B is an image of a stomach portion of the mouse obtained using the handheld device for photoacoustic microscopy of FIG. 7 and showing oxygen saturation level (the scale bar represents 300 μm)
Figure 19A:
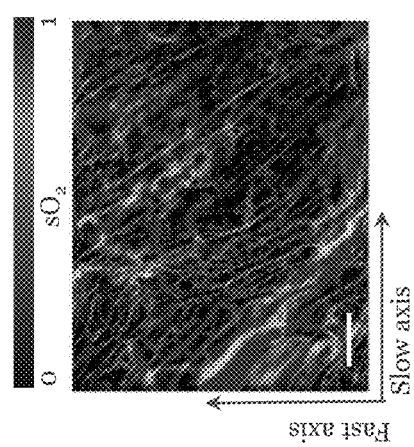
FIG. 19A is an image of an intestine portion of a mouse obtained using the handheld device for photoacoustic microscopy of FIG. 7 and showing oxygen saturation level (the scale bar represents 300 μm)

4. M' is used to transform the image $I_2$ to image $I'_2$
5. The repeated region of the image $I'_2$ and $I_1$ is overlapped to obtain a stitched image as shown in FIG. 15B In one example of compensation operation, the resonant mirror is driven by a sinusoidal voltage, which results in distortion in the fast axis. An interpolation of a sinusoidal function can be used to compensate for the distortion. A stainless-steel grating that has approximatively uniform widths is imaged using the device 702 and associated system. As shown in FIG. 16A, an image of the grating shows non-uniform width due to the trajectory distortion in the fast axis. After compensation, its original shape can be recovered, as shown in FIG. 16B. Specifically, the edge of the sample shown in FIG. 16B modifies the stretched shape due to the slow scanning speed. When the slow axis scans over a large range of 5 mm, the scanning trajectory becomes an arc. A stainless-steel sharp edge is used to measure the trajectory deformation. As shown in FIG. 17A, in a maximum-amplitude-projected image that has been compensated in the fast axis, the straight edge becomes an arc due to the slow axis trajectory. The deformation is calibrated to make the edge into a straight line as shown in FIG. 17B. The compensation method is further tested on straight human hair. FIG. 17C shows the raw image of the hair, which is curved dual to deformation. After compensation, the hair is recovered to a straight line, as shown in FIG. 17D. FIGS. 17A to 17D are obtained using a field of view of 1.7×5 mm², a pulse repetition rate of 500 kHz and a C-scan rate of 2 Hz.

Figure 18:
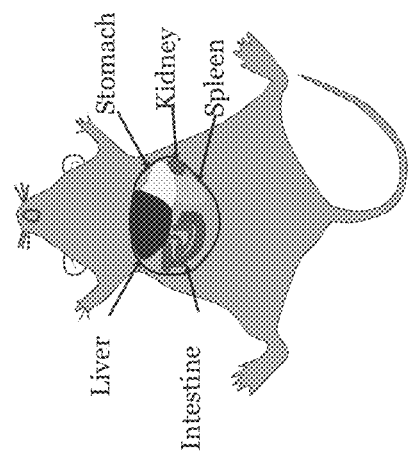
FIG. 18 is a schematic diagram of a mouse showing some of its internal organs.
Figure 19E:
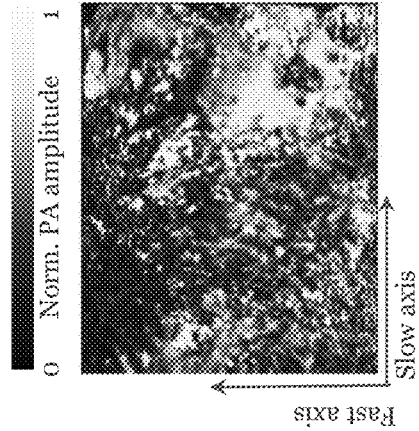
FIG. 19E is a photoacoustic image of a spleen portion of the mouse obtained using the handheld device for photoacoustic microscopy of FIG. 7 and showing vessel structure (the scale bar represents 300 μm)
Figure 19D:
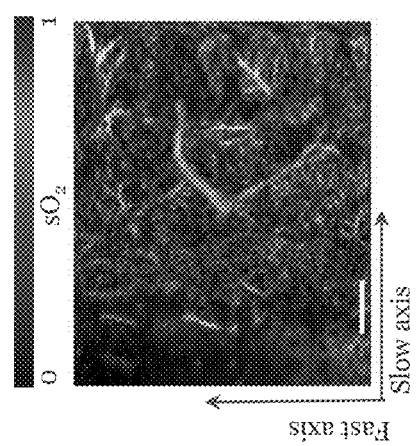
FIG. 19D is an image of a liver portion of the mouse obtained using the handheld device for photoacoustic microscopy of FIG. 7 and showing oxygen saturation level (the scale bar represents 300 μm)
Figure 19C:
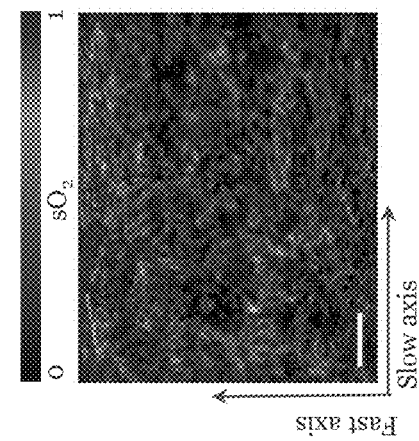
FIG. 19C is an image of a kidney portion of the mouse obtained using the handheld device for photoacoustic microscopy of FIG. 7 and showing oxygen saturation level (the scale bar represents 300 μm)

To verify the performance of the device 702 and the related system, a video-camera-mode imaging experiment is performed using the device 702. In this experiment the device 702 is used in the video-camera mode to image internal organs of a mouse during surgery. Multiple exposed organs of the mouse are examined. To minimize motion artifacts, a 4.6 Hz C-scan rate is used to image the tissues over 1.7×2 mm2. The step size is about 4.3 μm in the fast axis and about 7.8 μm in the slow axis. The curved scanning trajectory is calibrated. The A-line rate is 500 kHz for both the 532 nm and 558 nm wavelengths. The pulse energy is 70 to 80 nJ. The mouse is anesthetized with inhaled isoflurane at 1.5 mL/min. The abdomen skin is opened to expose the internal organs as shown in FIG. 18.

FIGS. 19A to 19E show the experimental results. As shown in FIGS. 19A to 19E, the microvasculature and oxygen saturation ($sO_2$) of the intestine (FIG. 19A), stomach (FIG. 19B), kidney (FIG. 19C), liver (FIG. 19D), and spleen (FIG. 19E) of the mouse are imaged. Although breathing and hand motion exist, the fast system can acquire high-resolution images with minimal motion artifacts or distortions. With the high imaging speed, a large area with different organs can be examined to locate regions of interest. These results demonstrate that the device 702 and related system of the invention can in this example rapidly acquire high-resolution images of the vessel microstructure and $sO_2$ with a super larger field of view, minimal motion artifacts, and a high signal-to-noise ratio of up to 29 dB. FIGS. 19B to 19E are obtained using a field of view of 1.7×2 mm², a pulse repetition rate of 500 kHz and a C-scan rate of 4.6 Hz.

Figure 20A:
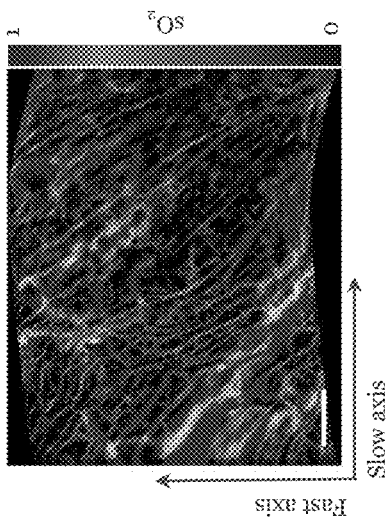
FIG. 20A is an image of an intestine portion of a mouse obtained using the handheld device for photoacoustic microscopy of FIG. 7 and showing oxygen saturation level, with compensation for distortion in the fast scan axis and without compensation for distortion in the slow scan axis (the scale bar represents 300 μm)
Figure 20B:
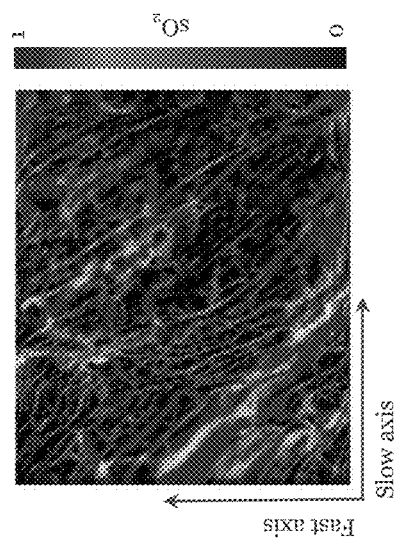
FIG. 20B is an image of the intestine portion of the mouse obtained using the handheld device for photoacoustic microscopy of FIG. 7 and showing oxygen saturation level, with compensation for distortion in both the fast scan axis and the slow scan axis (the scale bar represents 300 μm)

FIGS. 20A and 20B illustrate the calibration of the curved scanning trajectory is calibrated. Both FIGS. 20A and 20B illustrate sO2 image of the intestine of the mouse. FIG. 20A shows the image before compensation for the distortion in the slow axis. FIG. 20B shows the image after compensation for the distortion in the slow axis. In this example the maximal distortion only occupies 8% of the pixels in the fast axis.

Figure 21C:
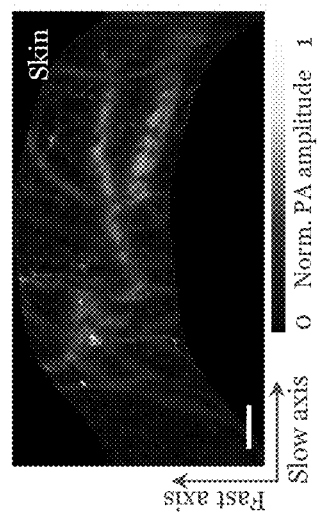
FIG. 21C is a photoacoustic image of a skin of a back portion of the mouse obtained using the handheld device for photoacoustic microscopy of FIG. 7 (the scale bar represents 320 μm)
Figure 21D:
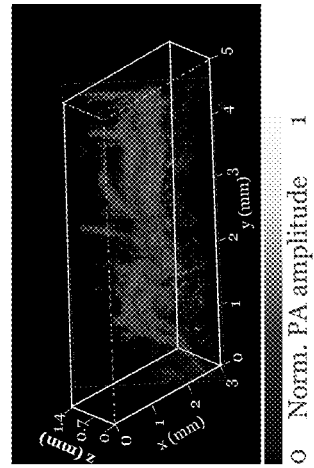
FIG. 21D is a 3D image of the skin of the back portion of the mouse obtained using the handheld device for photoacoustic microscopy of FIG. 7.
Figure 21A:
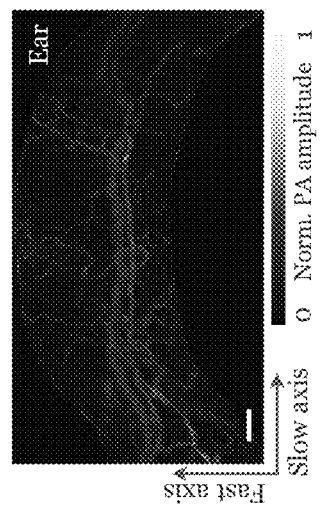
FIG. 21A is a photoacoustic image of an ear portion of a mouse obtained using the handheld device for photoacoustic microscopy of FIG. 7 (the scale bar represents 320 μm)
Figure 21B:
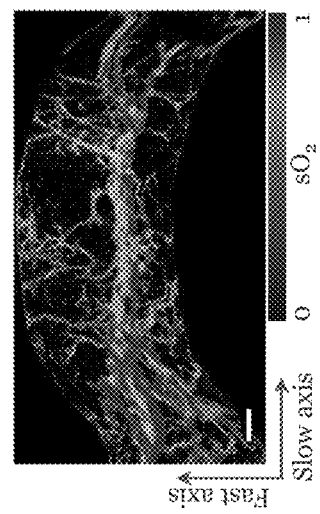
FIG. 21B is an image of the ear portion of the mouse obtained using the handheld device for photoacoustic microscopy of FIG. 7 and showing oxygen saturation level (the scale bar represents 320 μm)

To verify the performance of the device 702 and the related system, a high-speed in vivo imaging experiment is performed using the device 702. In this experiment the device 702 and system is used to acquire high-speed dual-wavelength images over millimeters-scale field of view, and the micro-vessel and oxygen saturation (sO2) in the mouse ear are imaged. The 532 nm and 558 nm laser pulse energies are 100 nJ and 90 nJ respectively. When the optical beam is focused 0.5 mm below the skin surface, the maximal permissible pulse energy is about 278 nJ, higher than the pulse energies used in the in vivo experiments. The laser pulse repetition rate (PRR) is 500 kHz for each wavelength. In the fast axis, the B-scan rate is 1288 Hz, the scanning range is 1.7 mm, and the average step size is about 4.3 µm. The step size in the slow axis is about 7.8 µm. The C-scan rate reaches 2 Hz with a FOV of about 1.7×5 mm². FIGS. 21A and 21B show representative vascular and sO2 images of the mouse ear (with scanning trajectories calibrated based on the above described compensation operation. At high imaging speed, blood flow (dynamic) in some vessels can be observed. The skin on the back of the mouse is also imaged. FIG. 21C show the photoacoustic image and FIG. 21D show the 3D vasculature image. These results show that device 702 and the related system can acquire high-speed in vivo images with high resolution, great sensitivity, and good stability.

To verify the performance of the device 702 and the related system, a high-speed heart imaging experiment is performed using the device 702 to monitor dynamic heart function in a heart failure of a mouse. In this experiment, the C-scan rate is 4.6 Hz over 1.7×2 mm² area. The step size is about 4.3 µm for the fast axis and about 7.8 µm for the slow axis. The pulse energy is 70 to 80 nJ. The heart wall is continuously imaged for about 22 seconds.

Figure 22:
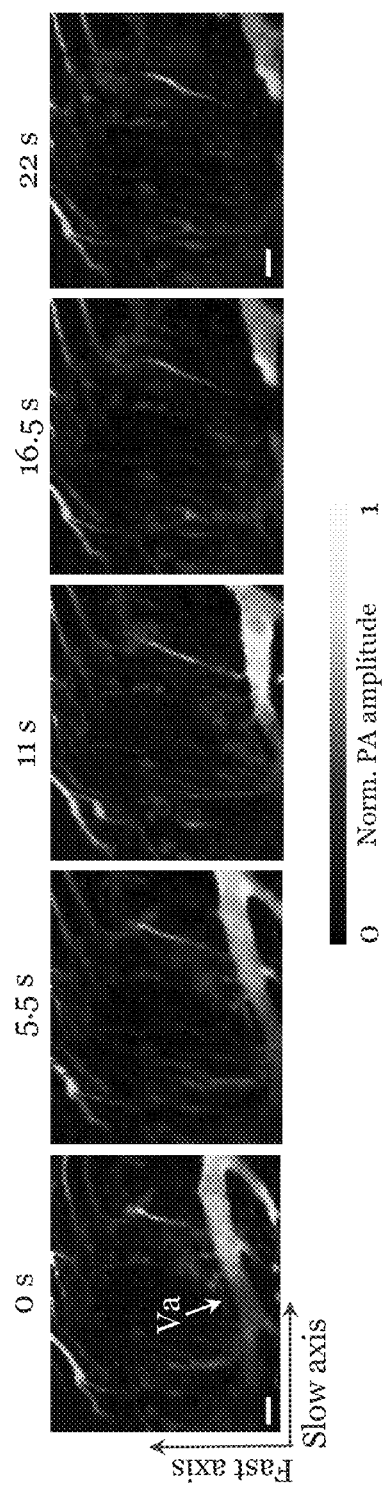
FIG. 22 shows a series of images of a heart wall of a mouse obtained using the handheld device for photoacoustic microscopy of FIG. 7 and illustrating the vascular structure during a heart failure process (the scale bar represents 200 μm)
Figure 23:
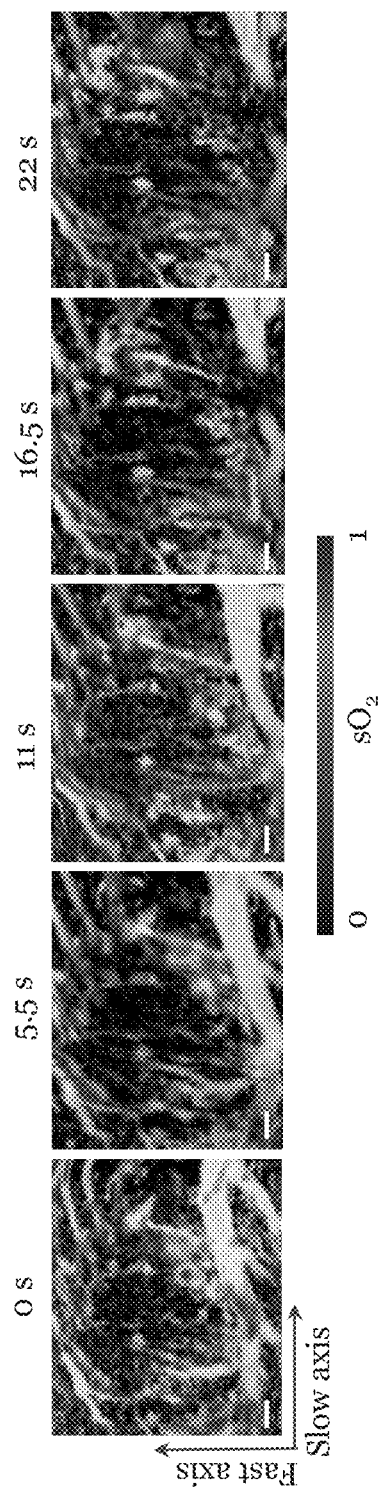
FIG. 23 shows a series of images of the heart wall of the mouse obtained using the handheld device for photoacoustic microscopy of FIG. 7 and illustrating the oxygen saturation level during the heart failure process (the scale bar represents 200 µm)
Figure 24:
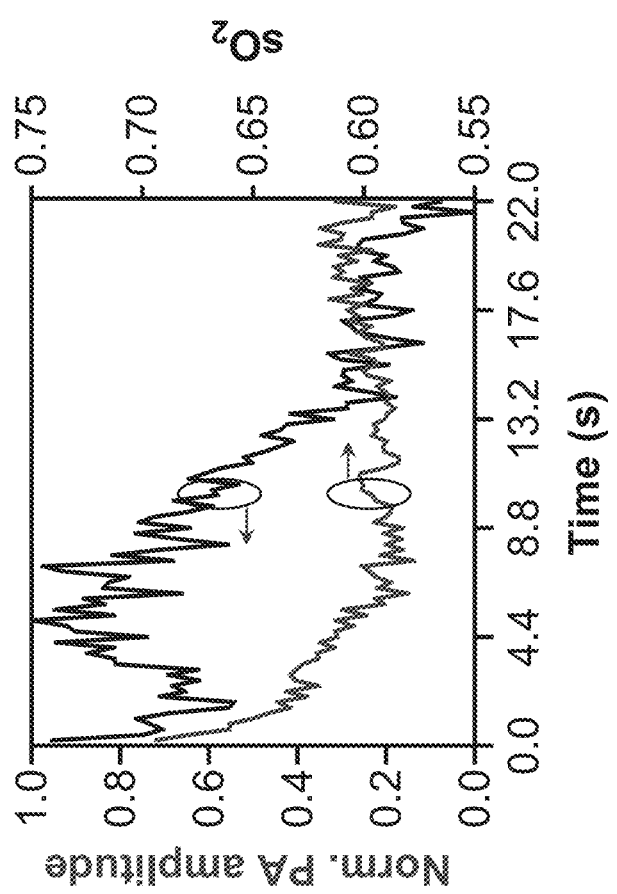
FIG. 24 is a graph showing variation of the average photoacoustic signal amplitude and the oxygen saturation level in a region of interest during the heart failure process.

FIGS. 22 to 24 show the experimental results. As shown in FIGS. 22 to 24, the fast C-scan rate enables dynamic imaging of the dying process without obvious motion artifacts. The vessel "Va" in FIG. 22 shows reduced and eventually ceased blood flow. The $sO_2$ in the vessel "Va" and the nearby region decreases fast as shown in FIG. 23. FIG. 24 shows the change in the average photoacoustic signal amplitude (normalized) and $sO_2$ in the region of interest. The average photoacoustic signal amplitude fluctuates in the first 7 seconds and then rapidly decreases. The average $sO_2$ decreases from the beginning and reaches an extremely low level (0.2 to 0.3) starting from about 6 seconds. This indicates that the low oxygen content is an important factor in this heart failure event. These results show that device 702 and the related system can be a useful tool for the study of heart diseases.

To verify the performance of the device 702 and the related system, a SLAM-mode imaging experiment is performed using the device 702. Via high-speed imaging, freehand scanning, and image stitching algorithm, the device 702 and system can work in the SLAM mode, in which the field of view can be enlarged to any freehand scanning range. In the experiment, the SLAM mode is used to image the brain of a mouse. To reduce image distortions, a 10 Hz C-scan rate to examine different regions in the brain cortex. The C-scan range is in 1.7×1.3 mm². In one experiment, a small lesion in a hemorrhagic stroke model is further localized. A focused high-power laser beam is applied induce a small hemorrhage spot in the brain of the mouse. In this experiment, the C-scan rate is 4.6 Hz, and one C-scan area is 1.5×2 mm².

Figure 25:
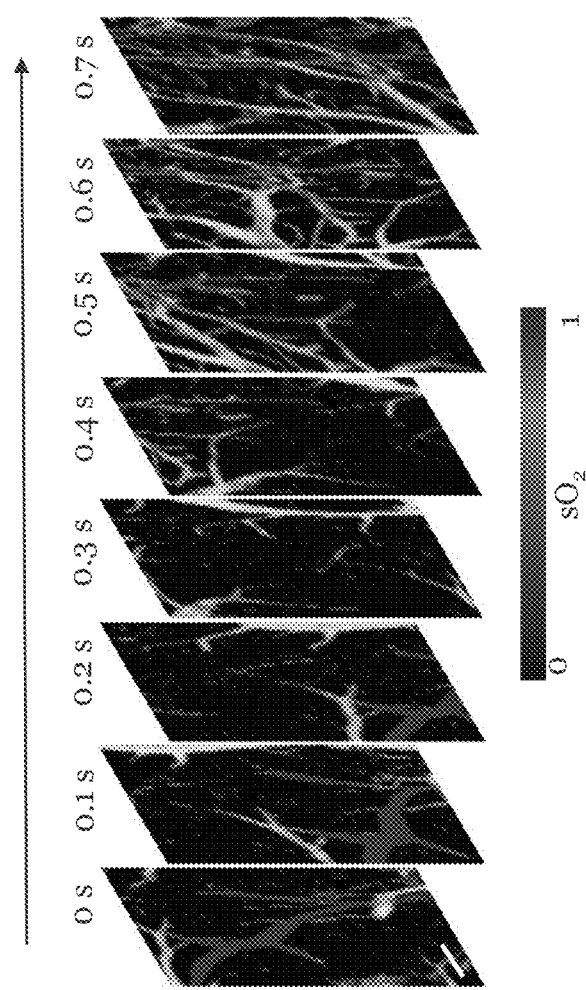
FIG. 25 shows a series of images of a brain portion of a mouse obtained using the handheld device for photoacoustic microscopy of FIG. 7 and illustrating the oxygen saturation level.
Figure 26:
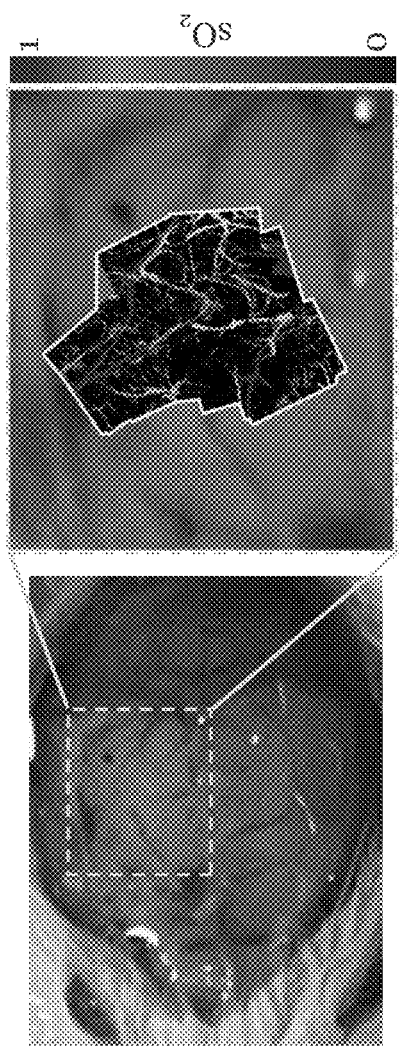
FIG. 26 illustrates an anatomical image (left) of a brain portion of a mouse and an image (right) of the brain portion of the mouse obtained using the handheld device for photoacoustic microscopy of FIG. 7 and illustrating oxygen saturation level (the scale bar represents 1 mm)
Figure 27:
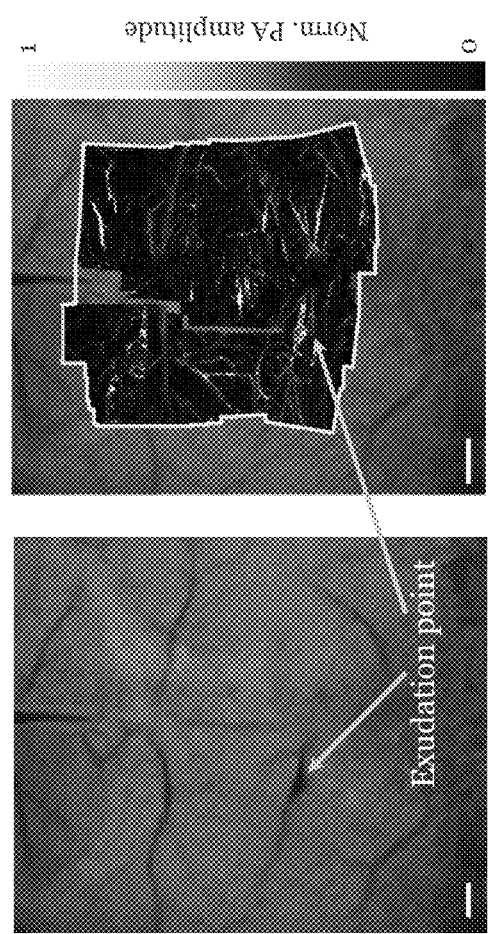
FIG. 27 illustrates an anatomical image (left) of a brain portion of a mouse and an image (right) of the brain portion of the mouse obtained using the handheld device for photoacoustic microscopy of FIG. 7 and illustrating oxygen saturation level with localization of a mini-hemorrhagic spot (the scale bar represents 1 mm).

FIGS. 25 to 27 illustrate the experimental results. FIG. 25 shows seven representative sO2 images of the brain. Consecutive frames have sufficient overlapped features and no obvious distortions from freehand scanning. As shown in FIG. 26, the images can be stitched together (based on the above described stitching operation) to reconstruct a large image. The boundary of the reconstructed image is highlighted in FIG. 26. The SLAM area is about 8.3 times of one C-scan area. To locate the lesion, the handheld probe 702 is scanned over a large region and a SLAM image is constructed. The stitched image is shown in FIG. 27. The lesion and its surrounding vessels can be identified in the reconstructed image. The field of view of the reconstructed image is about 13 times larger than one C-scan. These results show device 702 and the related system can enlarge the field of view without sacrificing imaging quality.

The above embodiments of the invention have enabled, among other things, freehand scanning photoacoustic microscopy which breaks the limit of the field of view. In some examples, the freehand scanning photoacoustic microscopy technique (system and/or method) can operate in a video-camera mode or a SLAM mode. In some examples, the video-camera-mode photoacoustic imaging is enabled by a handheld photoacoustic probe and a hybrid scanner. In some examples, the hybrid scanner, with a resonant mirror and a miniature galvo scanner, offers high-speed 2D scanning in millimeters-sized field of view. In some examples, the compact handheld probe can be freely moved to various anatomical sites. In some examples, the handheld high imaging speed with uncompromised resolution and sensitivity enables in vivo imaging of changes in blood perfusion and oxygen saturation. In some examples, the fast-imaging ability effectively reduces artifacts caused by hand motion or breathing.

The freehand scanning photoacoustic microscopy technique (system and/or method) in some embodiments may include one or more of the following advantages. For example, the freehand scanning photoacoustic microscopy technique (system and/or method) may enable an unrestricted or large field of view. For example, the freehand scanning photoacoustic microscopy technique (system and/or method) may include a handheld device, e.g., probe, that is compact, lightweight, and suitable for freehand scanning. For example, the freehand scanning photoacoustic microscopy technique (system and/or method) may include a hybrid scanner, driven by two drive mechanisms, which offers fast 2D scanning over a relatively large field of view to facilitate or ensure that the raw photoacoustic images have sufficient overlapped features. For example, the freehand scanning photoacoustic microscopy technique (system and/or method) may include a hybrid scanner that maintains the optical and acoustic alignment, isolates mechanical coupling between the fast and slow axes, and thus does not sacrifice the imaging quality. This is particularly important, although not essential, for robust image stitching. The freehand scanning photoacoustic microscopy technique (system and/or method) in some embodiments may obtain high-resolution images with dense micro-vessels in the overlapped regions, which offer abundant features for image stitching.

In some examples, in the SLAM mode, the freehand scanning speed is limited by the C-scan area and frame rate. To obtain sufficient overlapped features and minimize image distortion, the handheld probe may be scanned slower than the slow axis of the hybrid scanner. In one example the slow axis can scan at 9 to 13 mm/s. In some examples the SLAM-mode photoacoustic imaging is built on top of freehand scanning and a feature-based image stitching algorithm. The freehand scanning photoacoustic microscopy technique (system and/or method) can break the limit on field of view in conventional raster scanning but does not substantially sacrifice resolution, sensitivity, and imaging quality. In one example, the field of view is enlarged by 8.3 to 13 times than one C-scan imaging. The freehand scanning trajectory can be flexibly adjusted in 3D space, which enables large-scale lesion localization and tissue assessment.

It is believed that the freehand scanning photoacoustic microscopy technique (system and/or method) of the invention can be translated to or used in many preclinical and clinical applications.

Some embodiments of the invention may provide one or more of the following advantages. For example, some conventional handheld photoacoustic microscopy techniques cannot achieve real-time scanning whereas some embodiments of the invention can scan the sample with e.g., 10 Hz C-scan rates with millimeter scale. For example, some conventional handheld photoacoustic microscopy techniques cannot simultaneously satisfy the large field of view and high imaging speed whereas some embodiments of the invention can freely image regions of interest without obvious artifacts and field of view limitations. For example, some conventional handheld photoacoustic microscopy techniques cannot stitch images of different regions whereas some embodiments of the invention can scan stitch the images of different regions using image stitching operation to form an expanded field of view. For example, some conventional single-axis resonant-mirror-based handheld photoacoustic microscopy techniques suffer from bulk volume whereas some embodiments of the invention do not. For example, some conventional dual-axis resonant-mirror suffer from either the frequency coupling issue or limited field of view whereas some embodiments of the invention can decouple the frequency issue and enable a large field of view imaging. For example, some handheld photoacoustic microscopy techniques require more than one laser generator or source to measure sO2 whereas some embodiments of the invention can generate multiple wavelengths based on a single laser source or generator. Some embodiments of the invention may provide one or more advantages not specifically described.

Although not required, the embodiments described with reference to the Figures can be implemented as an application programming interface (API) or as a series of libraries for use by a developer or can be included within another software application, such as a terminal or computer operating system or a portable computing device operating system. Generally, as program modules include routines, programs, objects, components, and data files assisting in the performance of particular functions, the skilled person will understand that the functionality of the software application may or may not be distributed across a number of routines, objects, and/or components to achieve the same functionality desired herein.

It will also be appreciated that where the methods and systems of the invention are either wholly implemented by computing system or partly implemented by computing systems then any appropriate computing system architecture may be utilized. This will include stand-alone computers, network computers, dedicated or non-dedicated hardware devices. Where the terms "computing system" and "computing device" are used, these terms are intended to include but not limited to any appropriate arrangement of computer or information processing hardware capable of implementing the function described.

It will be appreciated by persons skilled in the art that variations and/or modifications may be made to the invention as shown in the specific embodiments to provide other embodiments of the invention. The described embodiments of the invention should therefore be considered in all respects as illustrative and not restrictive. Example optional features of some aspects of the invention are set forth in the summary section. Some embodiments of the invention may include one or more of these optional features (some of which are not specifically illustrated in the drawings). Some embodiments of the invention may lack one or more of these optional features (some of which are not specifically illustrated in the drawings). In some embodiments, data/image processing methods of the invention can be performed online in substantially real time. In some embodiments, data/image processing methods of the invention can be performed offline. The systems, devices, and methods of the invention may be used more generally for photoacoustic imaging, not limited to photoacoustic microscopy. One or more features of one embodiment may be combined with one or more features of another embodiment to provide further embodiments of the invention.

The invention claimed is:

1. A handheld device for photoacoustic microscopy, comprising:
    an optical assembly arranged to provide a light beam;
    a light beam scanner including
    a reflector arranged to reflect the light beam from the optical assembly to provide a reflected light beam to an object;
    a first drive mechanism operable to move the reflector relative to the optical assembly to move the reflected light beam relative to the object; and
    a second drive mechanism operable to move the reflector relative to the optical assembly to move the reflected light beam relative to the object;
    a transducer unit for detecting photoacoustic signals emitted by the object in response to receiving the reflected light beam; and
    a body with a handle portion and a head portion;
    wherein the reflector, the transducer unit, and at least part of the optical assembly are arranged in the head portion, wherein the head portion includes a chamber for receiving an acoustic coupling medium; and wherein at least the reflector and the transducer unit are arranged in the chamber.

2. The handheld device for photoacoustic microscopy of claim 1, wherein the reflector is arranged to reflect the photoacoustic signals from the object to the transducer unit.

3. The handheld device for photoacoustic microscopy of claim 1, wherein the first drive mechanism is a first type of drive mechanism, and the second drive mechanism is a second type of drive mechanism different from the first type.

4. The handheld device for photoacoustic microscopy of claim 1, wherein the first drive mechanism and the second drive mechanism are operable independently.

5. The handheld device for photoacoustic microscopy of claim 1, wherein the first drive mechanism is operable to rotate the reflector about a first axis to move the reflected light beam along a first scan axis.

6. The handheld device for photoacoustic microscopy of claim 5,
    wherein the second drive mechanism is operable to rotate the reflector about a second axis to move the reflected light beam along a second scan axis;
    wherein the first axis is different from the second axis, and the first scan axis is different from the second scan axis.

7. The handheld device for photoacoustic microscopy of claim 6,
    wherein the first axis and the second axis are substantially orthogonal; and/or
    wherein the first scan axis and the second scan axis are substantially orthogonal.

8. The handheld device for photoacoustic microscopy of claim 1,
wherein the first drive mechanism comprises one of a galvanometer-based drive mechanism and a resonance-based drive mechanism; and
wherein the second drive mechanism comprises another one of the galvanometer-based drive mechanism and the resonance-based drive mechanism.

9. The handheld device for photoacoustic microscopy of claim 8, wherein the galvanometer-based drive mechanism comprises a galvanometer-based motor.

10. The handheld device for photoacoustic microscopy of claim 8, wherein the reflector and the resonance-based drive mechanism are provided by a resonant mirror.

11. The handheld device for photoacoustic microscopy of claim 8, wherein the resonance-based drive mechanism comprises:
a magnetic arrangement operably coupled with the reflector; and
an electromagnet operable to magnetically interact with the magnetic arrangement to oscillate the reflector at a resonant frequency.

12. The handheld device for photoacoustic microscopy of claim 8, wherein the light beam scanner further comprises:
a frame to which the reflector is connected; and
a reflector support structure to which the frame is connected and including a space receiving the resonance-based drive mechanism.

13. The handheld device for photoacoustic microscopy of claim 12, wherein the frame is connected to the reflector support structure via one or more hinges.

14. The handheld device for photoacoustic microscopy of claim 12, wherein the galvanometer-based drive mechanism is operable to move the reflector support structure and the resonance-based drive mechanism to move the reflector relative to the optical assembly.

15. The handheld device for photoacoustic microscopy of claim 1, wherein the reflected light beam comprises a pulsed laser beam.

16. The handheld device for photoacoustic microscopy of claim 15, wherein the pulsed laser beam consists of laser pulses with a single wavelength.

17. The handheld device for photoacoustic microscopy of claim 15, wherein the pulsed laser beam comprises laser pulses with multiple wavelengths.

18. The handheld device for photoacoustic microscopy of claim 1,
wherein the light beam is a first light beam; and
wherein the optical assembly is arranged to manipulate a second light beam received from a light source to provide the first light beam.

19. The handheld device for photoacoustic microscopy of claim 18, wherein the optical assembly is arranged to focus or converge the second light beam such that the first light beam is a converging light beam.

20. The handheld device for photoacoustic microscopy of claim 1, wherein the optical assembly comprises:
an optical collimator;
a lens assembly; and
an optical-acoustic combiner arranged to reflect light beam to the reflector.

21. The handheld device for photoacoustic microscopy of claim 20, wherein the optical-acoustic combiner is acoustically-transparent to allow photoacoustic signals to pass.

22. The handheld device for photoacoustic microscopy of claim 21, wherein the optical-acoustic combiner is arranged to merge the light beam and the photoacoustic signals coaxially.

23. The handheld device for photoacoustic microscopy of claim 1, wherein the handle portion is hollow for receiving an optical fiber arranged to couple a light source with the optical assembly.

24. A photoacoustic microscopy system comprising:
the handheld device of claim 1;
a light source optically coupled with the handheld device; and
a controller for controlling operation of the first drive mechanism and the second drive mechanism of the handheld device.

25. The photoacoustic microscopy system of claim 24, wherein the photoacoustic microscopy system is operable in, at least, a first mode, in which the photoacoustic microscopy system is operated to image the same part of the object without moving the handheld device relative to the object, and a second mode, in which the photoacoustic microscopy system is operated to image different parts of the object with the handheld device moved relative to the object.

26. The photoacoustic microscopy system of claim 25, further comprising a data processing system for processing signals generated by the transducer unit as a result of the transducer unit receiving the photoacoustic signals, to generate photoacoustic-based images of the object.

27. The photoacoustic microscopy system of claim 26, wherein the data processing system comprises:
one or more processors; and
memory storing one or more programs configured to be executed by the one or more processors, the one or more programs including instructions for:
performing an image stitching operation to combine photoacoustic-based images of the object obtained in the second mode.

28. The photoacoustic microscopy system of claim 27, wherein the instructions for performing the image stitching operation comprises instructions for:
extracting, based on a feature detection algorithm, features in a first photoacoustic-based image and features in a second photoacoustic-based image, wherein a field of view of the first photoacoustic-based image partly overlaps with a field of view of the second photoacoustic-based image;
identifying features in the first photoacoustic-based image and features in the second photoacoustic-based image that correspond;
determining a transform function for transforming one or both of the first and second photoacoustic-based images such that the first and second photoacoustic-based images can be registered and stitched; and
registering and stitching the first and second photoacoustic-based images based on the determined transform function.

29. The microscopy system of claim 28, wherein the instructions for performing the image stitching operation further comprises instructions for:
detecting outlier features from the extracted features in the first photoacoustic-based image and/or extracted features in the second photoacoustic-based image; and
removing or ignoring the outlier features from subsequent processing such that the outlier features are not processed in the identifying of features that correspond.

30. The photoacoustic microscopy system of claim 27, wherein the one or more programs further comprise instructions for:
performing a compensation operation prior to performing the image stitching operation, the compensation operation comprising a scan trajectory distortion compensation operation to account for movement of the handheld device relative to the object in the second mode.

31. A photoacoustic microscopy system, comprising:
a handheld device including
an optical assembly arranged to provide a light beam;
a light beam scanner including
a reflector arranged to reflect the light beam from the optical assembly to provide a reflected light beam to an object,
a first drive mechanism operable to move the reflector relative to the optical assembly to move the reflected light beam relative to the object; and
a second drive mechanism operable to move the reflector relative to the optical assembly to move the reflected light beam relative to the object;
a transducer unit for detecting photoacoustic signals emitted by the object in response to receiving the reflected light beam;
a light source optically coupled with the handheld device;
a controller for controlling operation of the first drive mechanism and the second drive mechanism of the handheld device; and
a data processing system for processing signals generated by the transducer unit as a result of the transducer unit receiving the photoacoustic signals, to generate photoacoustic-based images of the object, wherein the photoacoustic microscopy system is operable in, at least, a first mode, in which the photoacoustic microscopy system is operated to image the same part of the object without moving the handheld device relative to the object, and a second mode, in which the photoacoustic microscopy system is operated to image different parts of the object with the handheld device moved relative to the object, wherein the data processing system comprises:
one or more processors; and
memory storing one or more programs configured to be executed by the one or more processors, the one or more programs including instructions for:
performing an image stitching operation to combine photoacoustic-based images of the object obtained in the second mode.

\* \* \* \* \*